United States Patent
Hashima et al.

(10) Patent No.: US 9,725,626 B2
(45) Date of Patent: Aug. 8, 2017

(54) BASE POLYMER FOR HOT-MELT ADHESIVE AGENT, AND HOT-MELT ADHESIVE AGENT

(71) Applicant: IDEMITSU KOSAN CO., LTD., Chiyoda-ku (JP)

(72) Inventors: Kazuhiro Hashima, Chiba (JP); Tomoaki Takebe, Chiba (JP); Yutaka Minami, Chiba (JP); Masao Inoue, Sodegaura (JP); Kenji Kobayashi, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 14/894,152

(22) PCT Filed: May 27, 2014

(86) PCT No.: PCT/JP2014/064019
§ 371 (c)(1),
(2) Date: Nov. 25, 2015

(87) PCT Pub. No.: WO2014/192767
PCT Pub. Date: Dec. 4, 2014

(65) Prior Publication Data
US 2016/0115360 A1    Apr. 28, 2016

(30) Foreign Application Priority Data

May 27, 2013    (JP) ................. 2013-111323

(51) Int. Cl.
| | | |
|---|---|---|
| C08F 110/06 | (2006.01) | |
| C09J 123/12 | (2006.01) | |
| C09J 5/06 | (2006.01) | |
| C09J 201/00 | (2006.01) | |
| A61L 15/24 | (2006.01) | |
| A61L 15/58 | (2006.01) | |
| C09J 5/00 | (2006.01) | |
| C08F 4/659 | (2006.01) | |

(52) U.S. Cl.
CPC ............ *C09J 123/12* (2013.01); *A61L 15/24* (2013.01); *A61L 15/58* (2013.01); *C08F 110/06* (2013.01); *C09J 5/00* (2013.01); *C09J 5/06* (2013.01); *C09J 201/00* (2013.01); *C08F 4/65908* (2013.01); *C08F 4/65912* (2013.01); *C09J 2201/61* (2013.01); *C09J 2400/263* (2013.01); *C09J 2423/00* (2013.01)

(58) Field of Classification Search
CPC ...................................................... C08F 110/06
See application file for complete search history.

(56) References Cited

U.S. PATENT DOCUMENTS

| | | | |
|---|---|---|---|
| 2004/0081795 | A1 | 4/2004 | Wang et al. |
| 2004/0115456 | A1 | 6/2004 | Kanderski et al. |
| 2005/0159566 | A1 | 7/2005 | Minami et al. |
| 2005/0171295 | A1 | 8/2005 | Kanamaru et al. |
| 2007/0043192 | A1 | 2/2007 | Okamoto et al. |

FOREIGN PATENT DOCUMENTS

| | | |
|---|---|---|
| CN | 101903463 A | 12/2010 |
| EP | 1 260 525 A1 | 11/2002 |
| EP | 1 498 432 A1 | 1/2005 |
| EP | 2 192 151 A1 | 6/2010 |
| EP | 2 527 508 A1 | 11/2012 |
| JP | 2006-503966 A | 2/2006 |
| JP | 2010-001367 A | 1/2010 |
| TW | 200404815 A | 4/2004 |
| WO | 03/087172 A1 | 10/2003 |
| WO | 03/091289 A1 | 11/2003 |
| WO | WO 2014/069604 A1 | 5/2014 |

OTHER PUBLICATIONS

International Search Report Issued Aug. 26, 2014 in PCT/JP2014/064019 Filed May 27, 2014.
Combined Chinese Office Action and Search Report issued Jan. 9, 2017 in Patent Application No. 201480030104.5.
Extended European Search Report issued Jan. 20, 2017 in Patent Application No. 14805049.5.

*Primary Examiner* — Wenwen Cai
(74) *Attorney, Agent, or Firm* — Oblon, McClelland, Maier & Neustadt, L.L.P.

(57) ABSTRACT

Provided is a hot-melt adhesive which satisfies both solidification rate and adhesiveness. A base polymer for a hot-melt adhesive which satisfies the following (1) and (2): (1) a modulus of elasticity in tension at 23° C. is 400 MPa or less; and (2) a semi-crystallization time at 23° C. is 20 minutes or less.

11 Claims, No Drawings

BASE POLYMER FOR HOT-MELT ADHESIVE AGENT, AND HOT-MELT ADHESIVE AGENT

TECHNICAL FIELD

The present invention relates to a base polymer for a hot-melt adhesive and a hot-melt adhesive using the same.

BACKGROUND ART

Many sanitary articles, particularly pants type diapers, pantiliners, and special cloths for use in cleaning, sterilization, and disinfection are composed of various multilayered materials according to the intended purposes thereof. For example, pants type diapers are composed of an inner layer having high liquid permeability, a fibrous inner layer (for example, a non-woven cloth) containing an absorbent material, for example, an ultra-absorbent material, and a plastic outer film through which water and all types of liquids do not permeate. In such a multilayered material, for the intended purposes thereof, the respective layers should be firmly bonded to one another so that interlayer peeling or displacement is not caused, further on the other hand, sufficiently favorable wearing feeling is provided. In such bonding, bonding by a hot-melt method in which bonding is carried out by melting a polymer by heat is used.

A hot-melt adhesive is a solvent-free adhesive and exhibits adhesiveness after the adhesive is melted by heating and coated onto an adherend, followed by cooling to solidify the adhesive. In recent years, a hot-melt adhesive has excellent high-speed coatability, quick curability, solvent-free property, barrier property, energy saving property, economic performance, and the like, and therefore, its use is expanded in various fields. In particular, the use of a polyolefin-based hot-melt adhesive having excellent heat stability is expanded. PTL 1 discloses a hot-melt adhesive composition using a high fluidity propylene-based polymer as a base polymer.

CITATION LIST

Patent Literature

PTL 1: WO 2003/091289

SUMMARY OF INVENTION

Technical Problem

A hot-melt adhesive has been demanded to have a high solidification rate when it is solidified by cooling to exhibit adhesiveness after it is melted by heating and coated onto an adherend, from the viewpoint of the productivity.

On the other hand, a hot-melt adhesive has also been demanded to have a function to firmly bond materials to each other. From the viewpoint of the adhesiveness, if the solidification rate is too high, the followability to an adherend is deteriorated, and therefore, a hot-melt adhesive has been demanded to have a moderate solidification rate.

An object of the present invention is to provide a hot-melt adhesive which satisfies both solidification rate and adhesiveness

Solution to Problem

According to the present invention, the following base polymer for a hot-melt adhesive, hot-melt adhesive, and bonding method are provided.

1. A base polymer for a hot-melt adhesive which satisfies the following (1) and (2):
   (1) a modulus of elasticity in tension at 23° C. is 400 MPa or less; and
   (2) a semi-crystallization time at 23° C. is 20 minutes or less.
2. The base polymer for a hot-melt adhesive according to the above 1, wherein the following (3) is satisfied:
   (3) an elongation at break at 23° C. is 150% or more and 1,000% or less.
3. The base polymer for a hot-melt adhesive according to the above 1 or 2, wherein a weight-average molecular weight is from 5,000 to 150,000.
4. The base polymer for a hot-melt adhesive according to any one of the above 1 to 3, containing a propylene homopolymer.
5. The base polymer for a hot-melt adhesive according to any one of the above 1 to 4, wherein the base polymer is a blend of 1 to 99 parts by mass of a propylene homopolymer (a) having a meso pentad fraction (mmmm) of 1 to 45 mol % and 99 to 1 part by mass of a propylene homopolymer (b) having a meso pentad fraction (mmmm) of 46 to 80 mol %, and the total amount of the propylene homopolymers (a) and (b) is 100 parts by mass.
6. A hot-melt adhesive, containing the base polymer for a hot-melt adhesive according to any one of the above 1 to 5.
7. The hot-melt adhesive according to the above 6, wherein the content of the base polymer for a hot-melt adhesive is from 1 to 90% by mass.
8. The hot-melt adhesive according to the above 6 or 7, further containing a tackifier resin and an oil.
9. A sanitary article obtained by using the hot-melt adhesive according to any one of the above 6 to 8.
10. A method for bonding a substrate to another substrate, including a step of melting the hot-melt adhesive according to any one of the above 6 to 8 and coating the adhesive onto at least one substrate, and a step of bonding the other substrate to the coated hot-melt adhesive.

Advantageous Effects of Invention

The hot-melt adhesive containing the base polymer for a hot-melt adhesive of the present invention not only has an excellent solidification rate, but also has excellent adhesiveness.

DESCRIPTION OF EMBODIMENTS

[Base Polymer for Hot-Melt Adhesive]

The "base polymer for a hot-melt adhesive" defined in this description is a polymer which is a component constituting a hot-melt adhesive and contributes to bonding, and also is a polymer which contributes to a cohesive force and an adhesion retaining force as an adhesive.

The solidification rate is defined as a time necessary for solidification until the hot-melt adhesive has a sufficient strength for forming a bond. A high solidification rate is important for an adhesive, and also important as a function that the bonded adherends are not peeled off from each other after solidification by cooling in the bonding line. From the viewpoint of the productivity, the solidification rate is preferably as high as possible.

From the viewpoint of the adhesive strength, it is considered to be preferred to use an adhesive having followability to an adherend, and moderate elongation and hardness.

The present inventors conducted intensive studies of an adhesive having moderate elongation and hardness while having a moderate solidification rate, and as a result, arrived the present invention.

Further, from the viewpoint of the adhesive strength when a film and a non-woven cloth are bonded to each other, it is considered to be preferred to use an adhesive which is soft on the grounds of the followability and the like of the adhesive to an adherend. On the other hand, from the viewpoint of the adhesive strength when non-woven cloths are bonded to each other, it is considered to be preferred to use an adhesive having moderate elongation and hardness. Accordingly, a suitable adhesive varies depending on the case where non-woven cloths are bonded to each other and the case where a film and a non-woven cloth are bonded to each other, respectively. However, in an actual production process, bonding of non-woven cloths and bonding of a film and a non-woven cloth are sometimes carried out by using the same adhesive, and therefore, an adhesive has been required to have both adhesiveness between non-woven cloths and adhesiveness between a film and a non-woven cloth.

The present inventors conducted intensive studies of an adhesive which is soft while having moderate elongation and hardness, and as a result, arrived the present invention.

The base polymer for a hot-melt adhesive of the present invention satisfies the following (1) and (2), and preferably further satisfies the following (3).

(1) A modulus of elasticity in tension at 23° C. is 400 MPa or less.

(2) A semi-crystallization time at 23° C. is 20 minutes or less.

(3) An elongation at break at 23° C. is 150% or more and 1,000% or less.

Preferred ranges of the above (1) to (3) are as follows.

(1') A modulus of elasticity in tension at 23° C. is 10 MPa or more and 400 MPa or less.

(2') A semi-crystallization time at 23° C. is 10 minutes or less.

(3') An elongation at break at 23° C. is 500% or more and 1,000% or less.

(Modulus of Elasticity in Tension)

From the viewpoint of the adhesiveness, the modulus of elasticity in tension is preferably lower, and the lower limit thereof is not particularly limited, and a measurement limit value becomes the lower limit. Specifically, the modulus of elasticity in tension is preferably 1 MPa or more, more preferably 5 MPa or more, further more preferably 10 MPa or more.

For example, in the case where a polyethylene film is used as the adherend, from the viewpoint of the followability of the hot-melt adhesive to the adherend, or from the viewpoint of the adhesiveness to the irregularities of the surface of the adherend, moderate softness is needed. From such a viewpoint, the modulus of elasticity in tension at 23° C. of the base polymer for a hot-melt adhesive of the present invention is 400 MPa or less, preferably 350 MPa or less, more preferably 300 MPa or less, further more preferably 250 MPa or less, still further more preferably 200 MPa or less, yet still further more preferably 150 MPa or less.

For example, in the case where a non-woven cloth is used as the adherend, from the viewpoint of the bleeding (seepage) of the hot-melt adhesive in the adherend, or from the viewpoint of the anchor effect on the irregularities of the surface of the adherend, moderate softness is needed. From such a viewpoint, the modulus of elasticity in tension at 23° C. of the base polymer for a hot-melt adhesive of the present invention is 400 MPa or less, preferably 350 MPa or less, more preferably 300 MPa or less, further more preferably 250 MPa or less, still further more preferably 200 MPa or less, yet still further more preferably 150 MPa or less.

The modulus of elasticity in tension of the base polymer for a hot-melt adhesive of the present invention is measured by the method described in Examples.

The modulus of elasticity in tension of the base polymer for a hot-melt adhesive of the present invention can be adjusted within a desired range by changing the polymerization conditions (a reaction temperature, a reaction time, a catalyst, or a promoter) of a propylene-based polymer (A), or by adding an additive, or by mixing two or more types of propylene-based polymers having different moduli of elasticity in tension.

(Semi-Crystallization Time)

The semi-crystallization time in the present invention refers to a time from the start of isothermal crystallization until the integral value of the calorific value becomes 50% when the integral value of the calorific value from the start of isothermal crystallization until the completion of crystallization is taken as 100%.

If the semi-crystallization time is too long, the solidification time of the hot-melt adhesive is too long (the solidification rate is low), and therefore, it is not suitable as the hot-melt adhesive. From such a viewpoint, the semi-crystallization time at 23° C. of the base polymer for a hot-melt adhesive of the present invention is 20 minutes or less, preferably 15 minutes or less, more preferably 12 minutes or less, further more preferably 10 minutes or less, particularly preferably 5 minutes or less. From the viewpoint of the solidification rate of the hot-melt adhesive, the semi-crystallization time is preferably shorter, and the lower limit thereof is not particularly limited, and a measurement limit value becomes the lower limit, but the measurement limit varies depending on the measurement device. The measurement limit value in a device to be used for the method described in Examples of this description is 1 minute. The semi-crystallization time at 23° C. of the base polymer for a hot-melt adhesive of the present invention is, for example, 1 minute or more, preferably 1.5 minutes or more.

The semi-crystallization time of the base polymer for a hot-melt adhesive of the present invention is measured by the method described in Examples.

The semi-crystallization time of the base polymer for a hot-melt adhesive of the present invention can be adjusted within a desired range by changing the polymerization conditions (a reaction temperature, a reaction time, a catalyst, or a promoter) of a propylene-based polymer (A), or by adding an additive, or by mixing two or more types of propylene-based polymers having different moduli of elasticity in tension.

(Elongation at Break)

From the viewpoint of the adhesive strength between a hot-melt adhesive and an adherend, in order to bring the hot-melt adhesive into close contact with the concave-convex surface of the adherend, it is preferred that the hot-melt adhesive is moderately soft. On the other hand, if the hot-melt adhesive is too soft, it is easily peeled off. From such a viewpoint, the elongation at break at 23° C. of the base polymer for a hot-melt adhesive of the present invention is preferably 150% or more, more preferably 300% or more, further more preferably 500% or more, still further more preferably 600% or more, and also preferably 1,000% or less, more preferably 800% or less, further more preferably 700% or less.

The elongation at break of the base polymer for a hot-melt adhesive of the present invention is measured by the method described in Examples.

The elongation at break of the base polymer for a hot-melt adhesive of the present invention can be adjusted within a desired range by changing the polymerization conditions (a reaction temperature, a reaction time, a catalyst, or a promoter) of a propylene-based polymer (A), or by adding an additive, or by mixing two or more types of propylene-based polymers having different elongations at break.

(Propylene-Based Polymer (A))

Further, the base polymer for a hot-melt adhesive of the present invention is not particularly limited as long as it satisfies the above (1) and (2), however, from the viewpoint of the adhesive strength between the non-woven cloths, it is preferred that the base polymer contains a propylene-based polymer (A) which satisfies the following (a) to (c). It is more preferred that the propylene-based polymer (A) further satisfies the following (d) to (f).

(a) [mmmm]=10 to 80 mol %

(b) a weight-average molecular weight (Mw)=10,000 to 150,000

(c) Mw/Mn≤2.5

(d) [rmrm]<2.5 mol %

(e) a melting point (Tm-D)=0 to 140° C.

(f) a glass transition temperature (Tg)=−20 to 10° C.

In the above formulae, [mmmm] represents a meso pentad fraction, and [rmrm] represents a racemic meso racemic meso pentad fraction.

The propylene-based polymer (A) to be used in the present invention is preferably a propylene homopolymer, but may be a copolymer between propylene and another olefin.

Examples of a comonomer other than propylene in the propylene-based copolymer include ethylene and α-olefins having 4 or more carbon atoms (preferably α-olefins having 4 to 20 carbon atoms). Specific examples of the α-olefin include 1-butene, 1-pentene, 4-methyl-1-pentene, 1-hexene, 1-octene, 1-decene, 1-dodecene, 1-tetradecene, 1-hexadecene, 1-octadecene, and 1-eicosene. In the present invention, among these, one type or two or more types can be used.

In the present invention, the meso pentad fraction [mmmm] and the racemic meso racemic meso pentad fraction [rmrm] are determined in accordance with the method proposed in "Macromolecules, 6, 925 (1973)" by A. Zambelli et al., and are a meso fraction and a racemic meso racemic meso fraction in a pentad unit in a polypropylene molecular chain measured with the signal of a methyl group in the $^{13}$C-NMR spectrum.

The measurement of the $^{13}$C-NMR spectrum was carried out using the following device under the following conditions.

Device: $^{13}$C-NMR spectrometer, JNM-EX400 series manufactured by JEOL, Ltd.

Method: proton complete decoupling method

Concentration: 220 mg/mL

Solvent: a mixed solvent of 1,2,4-trichlorobenzene and deuterated benzene at 90:10 (volume ratio)

Temperature: 130° C.

Pulse width: 45°

Pulse repetition time: 4 seconds

Accumulation: 10,000 times

<Calculation Formulae>

M=m/S×100

R=γ/S×100

S=Pββ+Pαβ+Pαγ

S: signal intensity of carbon atoms of side-chain methyl in all propylene units

Pββ: 19.8 to 22.5 ppm

Pαβ: 18.0 to 17.5 ppm

Pαγ: 17.7 to 17.1 ppm

γ: racemic pentad chain: 20.7 to 20.3 ppm m: meso pentad chain: 21.7 to 22.5 ppm Further, in the present invention, the weight-average molecular weight (Mw) and the number-average molecular weight (Mn) are a weight-average molecular weight and a number-average molecular weight in terms of polystyrene measured using the following device under the following conditions. The molecular weight distribution (Mw/Mn) is a value calculated from the weight-average molecular weight (Mw) and the number-average molecular weight (Mn).

<GPC Measuring Device>

Column: TOSO GMHHR-H(S)HT

Detector: RI detector for liquid chromatography, Waters 150 C.

<Measurement Conditions>

Solvent: 1,2,4-trichlorobenzene

Measurement temperature: 145° C.

Flow rate: 1.0 mL/min

Sample concentration: 2.2 mg/mL

Injection amount: 160 μL

Calibration curve: Universal Calibration

Analysis software: HT-GPC (ver. 1.0)

(a) Meso Pentad Fraction [Mmmm]

The meso pentad fraction [mmmm] of the propylene-based polymer (A) to be used in the present invention is preferably from 10 to 80 mol %, more preferably from 20 to 70 mol %, further more preferably from 25 to 65 mol %, still further more preferably more than 30 mol % and 65 mol % or less, yet still further more preferably more than 35 mol % and 60 mol % or less, most preferably more than 40 mol % and 60 mol % or less, from the viewpoint of the adhesive strength between non-woven cloths. The meso pentad fraction can be controlled by adjusting the monomer concentration or the reaction pressure.

(b) Weight-Average Molecular Weight (Mw)

The weight-average molecular weight of the propylene-based polymer (A) to be used in the present invention is preferably from 10,000 to 150,000, more preferably from 20,000 to 150,000, further more preferably from 20,000 to 120,000, still further more preferably from 20,000 to 100,000, yet still further more preferably from 20,000 to 80,000, most preferably from 30,000 to 60,000, from the viewpoint of the adhesive strength between non-woven cloths. The weight-average molecular weight can be controlled by appropriately adjusting the polymerization conditions (such as a propylene pressure and a polymerization time).

(c) Molecular Weight Distribution (Mw/Mn)

The molecular weight distribution (Mw/Mn) of the propylene-based polymer (A) to be used in the present invention is preferably 2.5 or less, more preferably 2.4 or less, further more preferably 2.3 or less, and also, for example, 1.2 or more, preferably 1.5 or more, from the viewpoint of the adhesive strength between non-woven cloths. The molecular weight distribution can be controlled by using a metallocene-based catalyst described later.

(d) Racemic Meso Racemic Meso Fraction [Rmrm]

The racemic meso racemic meso fraction [rmrm] of the propylene-based polymer (A) to be used in the present invention is preferably less than 2.5 mol %, more preferably less than 2.4 mol %, further more preferably less than 2.2 mol %, from the viewpoint of the adhesive strength between non-woven cloths. The [rmrm] can be controlled by using a metallocene-based catalyst described later.

(e) Melting Point (Tm-D)

The melting point (Tm-D) of the propylene-based polymer (A) to be used in the present invention is preferably from 0 to 140° C., more preferably from 20 to 120° C., further more preferably from 40 to 100° C., from the viewpoint of the adhesive strength between non-woven cloths.

In the present invention, the peak top of a peak observed on the highest temperature side in a melting endothermic curve obtained by using a differential scanning calorimeter (manufactured by PerkinElmer Co., Ltd., DSC-7), and keeping 10 mg of a sample in a nitrogen atmosphere at −10° C. for 5 minutes, and then raising the temperature at 10° C./min is defined as the melting point (Tm-D). The melting point can be controlled by appropriately adjusting the monomer concentration or the reaction pressure.

(f) Glass Transition Temperature (Tg)

The glass transition temperature (Tg) of the propylene-based polymer (A) to be used in the present invention is preferably from −20 to 10° C., more preferably from −10 to 10° C., further more preferably from −5 to 5° C., from the viewpoint of the adhesive strength between non-woven cloths. The glass transition temperature of the propylene-based polymer (A) is higher than that of a commercially available ethylene-based copolymer (Tg=−10 to −20° C.), and therefore, the blending amount a tackifier resin can be reduced as compared with the case where an ethylene-based copolymer is used as the base polymer.

(Production Method for Propylene-Based Polymer (A))

Examples of the production method for the propylene-based polymer (A) to be used in the present invention include a production method for a propylene homopolymer by homopolymerization of propylene using a metallocene catalyst and a production method for a propylene copolymer by copolymerization of propylene and ethylene and/or an α-olefin having 4 or more carbon atoms using a metallocene catalyst.

Examples of the metallocene-based catalyst include catalysts obtained by combining a transition metal compound containing one or two ligands selected from a cyclopentadienyl group, a substituted cyclopentadienyl group, an indenyl group, a substituted indenyl group, and the like as described in JP-A 58-19309, JP-A 61-130314, JP-A 3-163088, JP-A 4-300887, JP-A 4-211694, JP-T 1-502036, and the like, or a transition metal compound, in which the above ligand is geometrically controlled, with a promoter.

In the present invention, among the metallocene catalysts, a case where a catalyst contains a transition metal compound in which a ligand forms a crosslinked structure through a crosslinking group is preferred, and above all, a method using a metallocene catalyst obtained by combining a transition metal compound, in which a crosslinked structure is formed through two crosslinking groups, with a promoter is more preferred.

Specific examples of the method include a method of homopolymerizing propylene and a method of copolymerizing propylene and ethylene and/or an α-olefin having 4 or more carbon atoms, wherein the homopolymerization or the copolymerization is carried out in the presence of a polymerization catalyst containing (i) a transition metal compound represented by the general formula (I), and (ii) (ii-1) a component selected from a compound capable of reacting with the transition metal compound as the component (i) or a derivative thereof to form an ionic complex and (ii-2) an aluminoxane.

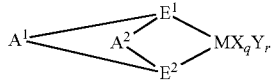

(I)

[In the formula, M represents a metal element of Groups 3 to 10 of the Periodic Table or a metal element of the lanthanoid series. $E^1$ and $E^2$ each represent a ligand selected from a substituted cyclopentadienyl group, an indenyl group, a substituted indenyl group, a heterocyclopentadienyl group, a substituted heterocyclopentadienyl group, an amide group, a phosphide group, a hydrocarbon group, and a silicon-containing group, and form a crosslinked structure through $A^1$ and $A^2$, and further, $E^1$ and $E^2$ may be the same as or different from each other; X represents a σ-bonding ligand, and when plural X's are present, plural X's may be the same as or different from each other and may be crosslinked with any other X, $E^1$, $E^2$, or Y; Y represents a Lewis base, and when plural Y's are present, plural Y's may be the same as or different from each other and may be crosslinked with any other Y, $E^1$, $E^2$, or X; $A^1$ and $A^2$ are each a divalent crosslinking group, which bonds two ligands, and each represent a hydrocarbon group having 1 to 20 carbon atoms, a halogen-containing hydrocarbon group having 1 to 20 carbon atoms, a silicon-containing group, a germanium-containing group, a tin-containing group, —O—, —CO—, —S—, —SO$_2$—, —Se—, —P(O)R$^1$—, —BR$^{1-}$, or —AlR$^1$—, wherein R$^1$ represents a hydrogen atom, a halogen atom, a hydrocarbon group having 1 to 20 carbon atoms, or a halogen-containing hydrocarbon group having 1 to 20 carbon atoms, and $A^1$ and $A^2$ may be the same as or different from each other; q is an integer of 1 to 5 and represents [(the atomic valence of M)−2]; and r represents an integer of 0 to 3].

In the above general formula (I), M represents a metal element of Groups 3 to 10 of the Periodic Table or a metal element of the lanthanoid series, and specific examples thereof include titanium, zirconium, hafnium, yttrium, vanadium, chromium, manganese, nickel, cobalt, palladium, and lanthanoid series metals. Among these, from the viewpoint of the olefin polymerization activity or the like, metal elements of Group 4 of the Periodic Table are preferred, and particularly, titanium, zirconium, and hafnium are preferred.

$E^1$ and $E^2$ each represent a ligand selected from a substituted cyclopentadienyl group, an indenyl group, a substituted indenyl group, a heterocyclopentadienyl group, a substituted heterocyclopentadienyl group, an amide group (—N<), a phosphine group (—P<), a hydrocarbon group [>CR—, >C<], and a silicon-containing group [>SiR—, >Si<] (wherein R is a hydrogen atom, or a hydrocarbon group having 1 to 20 carbon atoms or a heteroatom-containing group), and form a crosslinked structure through $A^1$ and $A^2$. $E^1$ and $E^2$ may be the same as or different from each other. As $E^1$ and $E^2$, a substituted cyclopentadienyl group, an indenyl group, and a substituted indenyl group are preferred. Examples of the substituent include a hydrocarbon group having 1 to 20 carbon atoms and a silicon-containing group.

Further, X represents a σ-bonding ligand, and in the case where plural X's are present, plural X's may be the same as or different from each other and may be crosslinked with any other X, $E^1$, $E^2$, or Y. Specific examples of this X include a halogen atom, a hydrocarbon group having 1 to 20 carbon atoms, an alkoxy group having 1 to 20 carbon atoms, an aryloxy group having 6 to 20 carbon atoms, an amide group having 1 to 20 carbon atoms, a silicon-containing group having 1 to 20 carbon atoms, a phosphide group having 1 to 40 carbon atoms, a sulfide group having 1 to 20 carbon atoms, and an acyl group having 1 to 20 carbon atoms.

Examples of the halogen atom include a chlorine atom, a fluorine atom, a bromine atom, and an iodine atom. Specific examples of the hydrocarbon group having 1 to 20 carbon atoms include an alkyl group such as a methyl group, an ethyl group, a propyl group, a butyl group, a hexyl group, a cyclohexyl group, and an octyl group; an alkenyl group such as a vinyl group, a propenyl group, and a cyclohexenyl group; an arylalkyl group such as a benzyl group, a phenylethyl group, and a phenylpropyl group; and an aryl group such as a phenyl group, a tolyl group, a dimethylphenyl group, a trimethylphenyl group, an ethylphenyl group, a propylphenyl group, a biphenyl group, a naphthyl group, a methylnaphthyl group, an anthracenyl group, and a phenanthryl group. Above all, an alkyl group such as a methyl group, an ethyl group, and a propyl group; and an aryl group such as a phenyl group are preferred.

Examples of the alkoxy group having 1 to 20 carbon atoms include an alkoxy group such as a methoxy group, an ethoxy group, a propoxy group, and a butoxy group; a phenylmethoxy group, and a phenylethoxy group. Examples of the aryloxy group having 6 to 20 carbon atoms include a phenoxy group, a methylphenoxy group, and a dimethylphenoxy group. Examples of the amide group having 1 to 20 carbon atoms include an alkylamide group such as a dimethylamide group, a diethylamide group, a dipropylamide group, a dibutylamide group, a dicyclohexylamide group, and a methylethylamide group; an alkenylamide group such as a divinylamide group, a dipropenylamide group, and a dicyclohexenylamide group; an arylalkylamide group such as a dibenzylamide group, a phenylethylamide group, and a phenylpropylamide group; and an arylamide group such as a diphenylamide group and a dinaphthylamide group.

Examples of the silicon-containing group having 1 to 20 carbon atoms include a mono-hydrocarbon-substituted silyl group such as a methylsilyl group and a phenylsilyl group; a dihydrocarbon-substituted silyl group such as a dimethylsilyl group and a diphenylsilyl group; a trihydrocarbon-substituted silyl group such as a trimethylsilyl group, a triethylsilyl group, a tripropylsilyl group, a tricyclohexylsilyl group, a triphenylsilyl group, a dimethylphenylsilyl group, a methyldiphenylsilyl group, a tritolylsilyl group, and a trinaphthylsilyl group; a hydrocarbon-substituted silyl ether group such as a trimethylsilyl ether group; a silicon-substituted alkyl group such as a trimethylsilylmethyl group; and a silicon-substituted aryl group such as a trimethylsilylphenyl group. Above all, a trimethylsilylmethyl group, a phenyldimethylsilylethyl group, and the like are preferred.

Examples of the phosphide group having 1 to 40 carbon atoms include a dialkyl phosphide group such as a dimethyl phosphide group, a diethyl phosphide group, a dipropyl phosphide group, a dibutyl phosphide group, a dihexyl phosphide group, a dicyclohexyl phosphide group, and a dioctyl phosphide group; a dialkenyl phosphide group such as a divinyl phosphide group, a dipropenyl phosphide group, and a dicyclohexenyl phosphide group; a bis(arylalkyl) phosphide group such as a dibenzyl phosphide group, a bis(phenylethyl) phosphide group, and a bis(phenylpropyl) phosphide group; and a diaryl phosphide group such as a diphenyl phosphide group, a ditolyl phosphide group, a bis(dimethylphenyl) phosphide group, a bis(trimethylphenyl) phosphide group, a bis(ethylphenyl) phosphide group, a bis(propylphenyl) phosphide group, a bis(biphenyl) phosphide group, a bis(naphthyl) phosphide group, a bis(methylnaphthyl) phosphide group, a bis(anthracenyl) phosphide group, and a bis(phenanthryl) phosphide group.

Examples of the sulfide group having 1 to 20 carbon atoms include an alkyl sulfide group such as a methyl sulfide group, an ethyl sulfide group, a propyl sulfide group, a butyl sulfide group, a hexyl sulfide group, a cyclohexyl sulfide group, and an octyl sulfide group; an alkenyl sulfide group such as a vinyl sulfide group, a propenyl sulfide group, and a cyclohexenyl sulfide group; an arylalkyl sulfide group such as a benzyl sulfide group, a phenylethyl sulfide group, and a phenylpropyl sulfide group; and an aryl sulfide group such as a phenyl sulfide group, a tolyl sulfide group, a dimethylphenyl sulfide group, a trimethylphenyl sulfide group, an ethylphenyl sulfide group, a propylphenyl sulfide group, a biphenyl sulfide group, a naphthyl sulfide group, a methylnaphthyl sulfide group, an anthracenyl sulfide group, and a phenanthryl sulfide group.

Examples of the acyl group having 1 to 20 carbon atoms include a formyl group; an alkylacyl group such as an acetyl group, a propionyl group, a butyryl group, a valeryl group, a palmitoyl group, a stearoyl group, and an oleoyl group; an arylacyl group such as a benzoyl group, a toluoyl group, a salicyloyl group, a cinnamoyl group, a naphthoyl group, and a phthaloyl group; and an oxalyl group, a malonyl group, and a succinyl group, which are derived from oxalic acid, malonic acid, and succinic acid, each being a dicarboxylic acid, respectively.

On the other hand, Y represents a Lewis base, and in the case where plural Y's are present, plural Y's may be the same as or different from each other and may be crosslinked with any other Y, $E^1$, $E^2$, or X. Specific examples of the Lewis base represented by Y include amines, ethers, phosphines, and thioethers.

Examples of the amines include amines having 1 to 20 carbon atoms, and specific examples thereof include alkylamines such as methylamine, ethylamine, propylamine, butylamine, cyclohexylamine, methylethylamine, dimethyl amine, diethylamine, dipropylamine, dibutylamine, dicyclohexylamine, and methylethylamine; alkenylamines such as vinylamine, propenylamine, cyclohexenylamine, divinylamine, dipropenylamine, and dicyclohexenylamine; arylalkylamines such as phenylamine, phenylethylamine, and phenylpropylamine; and arylamines such as diphenylamine and dinaphthylamine.

Examples of the ethers include aliphatic monoether compounds such as methyl ether, ethyl ether, propyl ether, isopropyl ether, butyl ether, isobutyl ether, n-amyl ether, and isoamyl ether; aliphatic mixed ether compounds such as methylethyl ether, methylpropyl ether, methylisopropyl ether, methyl-n-amyl ether, methylisoamyl ether, ethylpropyl ether, ethylisopropyl ether, ethylbutyl ether, ethylisobutyl ether, ethyl-n-amyl ether, and ethylisoamyl ether; aliphatic unsaturated ether compounds such as vinyl ether, allyl ether, methylvinyl ether, methylallyl ether, ethylvinyl ether, and ethylallyl ether; aromatic ether compounds such as anisole, phenetole, phenyl ether, benzyl ether, phenylbenzyl ether, α-naphthyl ether, and β-naphthyl ether; and cyclic ether compounds such as ethylene oxide, propylene oxide, trimethylene oxide, tetrahydrofuran, tetrahydropyran, and dioxane.

Examples of the phosphines include phosphines having 1 to 30 carbon atoms. Specific examples thereof include alkyl phosphines such as monohydrocarbon-substituted phosphines such as methyl phosphine, ethyl phosphine, propyl phosphine, butyl phosphine, hexyl phosphine, cyclohexyl phosphine, and octyl phosphine; dihydrocarbon-substituted phosphines such as dimethyl phosphine, diethyl phosphine, dipropyl phosphine, dibutyl phosphine, dihexyl phosphine, dicyclohexyl phosphine, and dioctyl phosphine; and trihydrocarbon-substituted phosphines such as trimethyl phosphine, triethyl phosphine, tripropyl phosphine, tributyl phosphine, trihexyl phosphine, tricyclohexyl phosphine, and trioctyl phosphine; monoalkenyl phosphines such as vinyl phosphine, propenyl phosphine, and cyclohexenyl phosphine; dialkenyl phosphines in which two hydrogen atoms of phosphine are each substituted with alkenyl; trialkenyl phosphines in which three hydrogen atoms of phosphine are each substituted with alkenyl; and arylphosphines such as arylalkyl phosphines such as benzyl phosphine, phenylethyl phosphine, and phenylpropyl phosphine; diarylalkyl phosphines or aryldialkyl phosphines in which three hydrogen atoms of phosphine are each substituted with aryl or alkenyl; phenyl phosphine, tolyl phosphine, dimethylphenyl phosphine, trimethylphenyl phosphine, ethylphenyl phosphine, propylphenyl phosphine, biphenyl phosphine, naphthyl phosphine, methylnaphthyl phosphine, anthracenyl phosphine, and phenanthryl phosphine; di(alkylaryl) phosphines in which two hydrogen atoms of phosphine are each substituted with alkylaryl; and tri(alkylaryl) phosphines in which three hydrogen atoms of phosphine are each substituted with alkylaryl. Examples of the thioethers include the above-mentioned sulfides.

Next, $A^1$ and $A^2$ are each a divalent crosslinking group, which bonds two ligands, and each represent a hydrocarbon group having 1 to 20 carbon atoms, a halogen-containing hydrocarbon group having 1 to 20 carbon atoms, a silicon-containing group, a germanium-containing group, a tin-containing group, —O—, —CO—, —S—, —SO$_2$—, —Se—, —NR$^1$—, —PR$^1$—, —P(O)R$^1$—, —BR$^1$—, or —AlR$^1$—, wherein $R^1$ represents a hydrogen atom, a halogen atom, a hydrocarbon group having 1 to 20 carbon atoms, or a halogen-containing hydrocarbon group having 1 to 20 carbon atoms, and $A^1$ and $A^2$ may be the same as or different from each other. Examples of such a crosslinking group include a group represented by the following general formula (II).

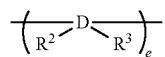
(II)

(D is carbon, silicon, or tin. $R^2$ and $R^3$ are each a hydrogen atom or a hydrocarbon group having 1 to 20 carbon atoms, and may be the same as or different from each other, or may be bonded to each other to form a ring structure. e represents an integer of 1 to 4.)

Specific examples thereof include a methylene group, an ethylene group, an ethylidene group, a propylidene group, an isopropylidene group, a cyclohexylidene group, a 1,2-cyclohexylene group, a vinylidene group (CH$_2$=C=), a dimethylsilylene group, a diphenylsilylene group, a methylphenylsilylene group, a dimethylgermylene group, a dimethylstannylene group, a tetramethyldisilylene group, and a diphenyldisilylene group. Among these, an ethylene group, an isopropylidene group, and a dimethylsilylene group are preferred.

q is an integer of 1 to 5 and represents [(the atomic valence of M)-2], and r represents an integer of 0 to 3.

Specific examples of the transition metal compound represented by the general formula (I) include the specific examples described in WO 02/16450 as preferred examples also in the present invention.

More preferred specific examples thereof include (1,2'-dimethylsilylene) (2,1'-dimethylsilylene)bis(indenyl)zirconium dichloride, (1,2'-dimethylsilylene) (2,1'-dimethylsilylene) (indenyl) (3-trimethylsilylmethylindenyl)zirconium dichloride, and (1,2'-dimethylsilylene) (2, 1'-dimethylsilylene)bis(3-trimethylsilylmethylindenyl)zirconium dichloride.

Next, any compound can be used as the component (ii-1) in the components (ii) as long as it is a compound which can be reacted with the transition metal compound as the component (i) described above to form an ionic complex, however, a compound represented by the following general formula (III) or (IV) can be preferably used:

(III)

(IV)

wherein, $L^2$ is $M^2$, $R^{11}R^{12}M^3$, $R^{13}{}_3C$, or $R^{14}M^3$.

In the above general formulae (III) and (IV), $L^1$ represents a Lewis base, $[Z]^-$ represents a non-coordinating anion $[Z^1]^-$ or $[Z^2]^-$.

$[Z^1]^-$ represents an anion in which plural groups are bonded to an element, that is, $[M^1G^1G^2 \ldots G^f]^-$. Here, $M^1$ represents an element of Groups 5 to 15 of the Periodic Table, preferably an element of Groups 13 to 15 of the Periodic Table. $G^1$ to $G^f$ each represent a hydrogen atom, a halogen atom, an alkyl group having 1 to 20 carbon atoms, a dialkylamino group having 2 to 40 carbon atoms, an alkoxy group having 1 to 20 carbon atoms, an aryl group having 6 to 20 carbon atoms, an aryloxy group having 6 to 20 carbon atoms, an alkylaryl group having 7 to 40 carbon atoms, an arylalkyl group having 7 to 40 carbon atoms, a halogen-substituted hydrocarbon group having 1 to 20 carbon atoms, an acyloxy group having 1 to 20 carbon atoms, an organic metalloid group, or a heteroatom-containing hydrocarbon group having 2 to 20 carbon atoms. Two or more groups of $G^1$ to $G^f$ may form a ring. f represents an integer of [(the atomic valence of the central metal $M^1$)+1]).

$[Z^2]^-$ represents a conjugate base of a Bronsted acid alone in which the logarithm (pKa) of an inverse number of an acid dissociation constant is −10 or less or a combination of a Bronsted acid and a Lewis acid, or a conjugate base of an acid generally defined as an ultrastrong acid. Further, a Lewis base may be coordinated.

$R^{10}$ represents a hydrogen atom, an alkyl group having 1 to 20 carbon atoms, an aryl group having 6 to 20 carbon atoms, an alkylaryl group, or an arylalkyl group.

$R^{11}$ and $R^{12}$ each represent a cyclopentadienyl group, a substituted cyclopentadienyl group, an indenyl group, or a fluorenyl group.

$R^{13}$ represents an alkyl group having 1 to 20 carbon atoms, an aryl group, an alkylaryl group, or an arylalkyl group.

$R^{14}$ represents a large cyclic ligand such as tetraphenylporphyrin or phthalocyanine. k is the ionic valence of each of $[L^1-R^{10}]$ and $[L^2]$, and represents an integer of 1 to 3, a represents an integer of 1 or more, and b is (k×a). $M^2$ includes an element of Groups 1 to 3, 11 to 13, and 17 of the Periodic Table, and $M^3$ represents an element of Groups 7 to 12 of the Periodic Table.

Here, specific examples of $L^1$ include ammonia, amines such as methylamine, aniline, dimethylamine, diethylamine, N-methylaniline, diphenylamine, N,N dimethylaniline, trimethylamine, triethylamine, tri-n-butylamine, methyldiphenylamine, pyridine, p-bromo-N,N-dimethylaniline, and p-nitro-N,N-dimethylaniline, phosphines such as triethylphosphine, triphenylphosphine, and diphenylphosphine, thioethers such as tetrahydrothiophene, esters such as ethyl benzoate, and nitriles such as acetonitrile and benzonitrile.

Specific examples of $R^{10}$ include hydrogen, a methyl group, an ethyl group, a benzyl group, and a trityl group. Specific examples of $R^{11}$ and $R^{12}$ include a cyclopentadienyl group, a methylcyclopentadienyl group, an ethylcyclopentadienyl group, and a pentamethylcyclopentadienyl group.

Specific examples of $R^{13}$ include a phenyl group, a p-tolyl group, and a p-methoxyphenyl group. Specific examples of $R^{14}$ include teteraphenylporphine, phthalocyanine, allyl, and metallyl. Specific examples of $M^2$ include Li, Na, K, Ag, Cu, Br, I, and $I_3$. Specific examples of $M^3$ include Mn, Fe, Co, Ni, and Zn.

Further, in $[Z^1]^-$, that is, $[M^1G^1G^2 \ldots G^f]$, specific examples of $M^1$ include B, Al, Si, P, As, and Sb, and preferred examples thereof include B and Al. Specific examples of $G^1$, $G^2$ to $G^f$ include a dialkylamino group such as a dimethylamino group and a diethylamino group, an alkoxy group or an aryloxy group such as a methoxy group, an ethoxy group, an n-butoxy group, and a phenoxy group, a hydrocarbon group such as a methyl group, an ethyl group, an n-propyl group, an isopropyl group, an n-butyl group, an isobutyl group, an n-octyl group, an n-eicosyl group, a phenyl group, a p-tolyl group, a benzyl group, a 4-t-butyl-phenyl group, and a 3,5-dimethylphenyl group, a halogen atom such as fluorine, chlorine, bromine, and iodine, a heteroatom-containing hydrocarbon group such as a p-fluorophenyl group, a 3,5-difluorophenyl group, a pentachlorophenyl group, a 3,4,5-trifluorophenyl group, a pentafluorophenyl group, a 3,5-bis(trifluoromethyl)phenyl group, and a bis(trimethylsilyl)methyl group, and an organic metalloid group such as a pentamethylantimony group, a trimethylsilyl group, a trimethylgermyl group, a diphenylarsine group, a dicyclohexylantimony group, and diphenylboron.

Also, specific examples of the non-coordinating anion, that is, the conjugate base $[Z^2]^-$ of a Bronsted acid alone having a pKa of −10 or less or a combination of a Bronsted acid with a Lewis acid include a trifluoromethanesulfonic acid anion $(CF_3SO_3)^-$, a bis(trifluoromethanesulfonyl)methyl anion, a bis(trifluoromethanesulfonyl)benzyl anion, bis(trifluoromethanesulfonyl)amide, a perchloric acid anion $(ClO_4)^-$, a trifluoroacetic acid anion $(CF_3CO_2)^-$, a hexafluoroantimony anion $(SbF_6)^-$, a fluorosulfonic acid anion $(FSO_3)^-$, a chlorosulfonic acid anion $(ClSO_3)^-$, a fluorosulfonic acid anion/an antimony pentafluoride $(FSO_3/SbF_5)^-$, a fluorosulfonic acid anion/arsenic pentafluoride $(FSO_3/AsF_5)^-$, and trifluoromethanesulfonic acid/antimony pentafluoride $(CF_3SO_3/SbF_5)^-$.

Specific examples of the ionic compound which is reacted with the transition metal compound as the component (i) described above to form an ionic complex, that is, the compound as the component (ii-1) include triethylammonium tetraphenylborate, tri-n-butylammonium tetraphenylborate, trimethylammonium tetraphenylborate, tetraethylammonium tetraphenylborate, methyl(tri-n-butyl)ammonium tetraphenylborate, benzyl(tri-n-butyl)ammonium tetraphenylborate, dimethyldiphenylammonium tetraphenylborate, triphenyl(methyl)ammonium tetraphenylborate, trimethylanilinium tetraphenylborate, methylpyridinium tetraphenylborate, benzylpyridinium tetraphenylborate, methyl(2-cyanopyridinium) tetraphenylborate, triethylammonium tetrakis(pentafluorophenyl)borate, tri-n-butyl ammonium tetrakis(pentafluorophenyl)borate, triphenylammonium tetrakis(pentafluorophenyl)borate, tetra-n-butylammonium tetrakis(pentafluorophenyl)borate, tetraethylammonium tetrakis(pentafluorophenylborate), benzyl(tri-n-butyl)ammonium tetrakis(pentafluorophenyl)borate, methyldiphenylammonium tetrakis(pentafluorophenyl)borate, triphenyl(methyl)ammonium tetrakis(pentafluorophenyl)borate, methylanilinium tetrakis(pentafluorophenyl)borate, dimethylanilinium tetrakis(pentafluorophenyl)borate, trimethylanilinium tetrakis(pentafluorophenyl)borate, methylpyridinium tetrakis(pentafluorophenyl)borate, benzylpyridinium tetrakis(pentafluorophenyl)borate, methyl(2-cyanopyridinium) tetrakis(pentafluorophenyl)borate, benzyl(2-cyanopyridinium) tetrakis(pentafluorophenyl)borate, methyl(4-cyanopyridinium) tetrakis(pentafluorophenyl)borate, triphenylphosphonium tetrakis(pentafluorophenyl)borate, dimethylanilinium tetrakis[bis(3, 5-ditrifluoromethyl)phenyl]borate, ferrocenium tetraphenylborate, silver tetraphenylborate, trityl tetraphenylborate, tetraphenylporphyrinmanganese tetraphenylborate, ferrocenium tetrakis(pentafluorophenyl)borate, (1,1'-dimethylferrocenium) tetrakis(pentafluorophenyl)borate, decamethylferrocenium tetrakis(pentafluorophenyl)borate, silver tetrakis(pentafluorophenyl)borate, trityl tetrakis(pentafluorophenyl)borate, lithium tetrakis(pentafluorophenyl)borate, sodium tetrakis(pentafluorophenyl)borate, tetraphenylporphyrinmanganese tetrakis(pentafluorophenyl)borate, silver tetrafluoroborate, silver hexafluorophosphate, silver hexafluoroarsenate, silver perchlorate, silver trifluoroacetate, and silver trifluoromethanesulfonate.

As (ii-1), one type may be used or two or more types may be used in combination.

On the other hand, examples of the aluminoxane as the component (ii-2) include a chain aluminoxane represented by the general formula (V):

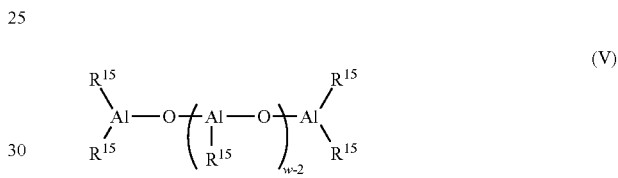

wherein $R^{15}$ represents a hydrocarbon group having 1 to 20 carbon atoms, preferably 1 to 12 carbon atoms such as an alkyl group, an alkenyl group, an aryl group, or an arylalkyl group or a halogen atom; and w represents an average polymerization degree and is an integer of usually 2 to 50, preferably 2 to 40, provided that the respective $R^{15}$'s may be the same as or different from each other) and a cyclic aluminoxane represented by the general formula (VI):

wherein $R^{15}$ and w are the same as those in the above general formula (V).

Examples of the production method for the aluminoxane described above include a method in which alkylaluminum is brought into contact with a condensing agent such as water, but a means thereof is not particularly limited, and they may be reacted according to a known method. Examples of the method include (1) a method in which an organic aluminum compound is dissolved in an organic solvent, and then the resulting solution is brought into contact with water, (2) a method in which an organic aluminum compound is first added when carrying out polymerization, and then water is added thereto, (3) a method in which an organic aluminum compound is reacted with crystal water contained in a metal salt or the like, or water adsorbed on an inorganic substance or an organic substance, and (4) a method in which trialkylaluminum is reacted with tetraalkyldialuminoxane and the reaction product is further reacted with water. The aluminoxane may be an aluminoxane which is insoluble in toluene.

Among these aluminoxanes, one type may be used or two or more types may be used in combination.

It is desired that the use proportion of the catalyst component (i) to the catalyst component (ii) is in the range of preferably 10:1 to 1:100, more preferably 2:1 to 1:10 in terms of molar ratio when the compound (ii-1) is used as the catalyst component (ii), and if it deviates from the above range, the catalyst cost per unit mass of the polymer increases, so that it is not practical. When the compound (ii-2) is used, it is desired that the use proportion is in the range of preferably 1:1 to 1:1,000,000, more preferably 1:10 to 1:10,000 in terms of molar ratio. If it deviates from the above range, the catalyst cost per unit mass of the polymer increases, so that it is not practical. Further, as the catalyst component (ii), (ii-1) and (ii-2) can be used alone or two or more types can be used in combination.

In the polymerization catalyst in the above production method, an organic aluminum compound as a component (iii) can be used in addition to the component (i) and the component (ii) described above.

Here, as the organic aluminum compound serving as the component (iii), a compound represented by the general formula (VII) is used:

$$R^{16}_v AlJ_{3-v} \quad (VII)$$

wherein, $R^{16}$ represents an alkyl group having 1 to 10 carbon atoms, J represents a hydrogen atom, an alkoxy group having 1 to 20 carbon atoms, an aryl group having 6 to 20 carbon atoms, or a halogen atom, and v is an integer of 1 to 3.

Specific examples of the compound represented by the above general formula (VII) include trimethylaluminum, triethylaluminum, triisopropylaluminum, triisobutylaluminum, dimethylaluminum chloride, diethylaluminum chloride, methylaluminum dichloride, ethylaluminum dichloride, dimethylaluminum fluoride, diisobutylaluminum hydride, diethylaluminum hydride, and ethylaluminum sesquichloride.

Among these organic aluminum compounds, one type may be used or two or more types may be used in combination.

In the production method, preliminary contact can also be carried out using the component (i), the component (ii), and the component (iii) described above. The preliminary contact can be carried out by, for example, bringing the component (ii) into contact with the component (i), but the method is not particularly limited, and a known method can be used. This preliminary contact is effective in the reduction in the catalyst cost due to the improvement of the catalyst activity, the reduction in the use proportion of the component (ii) which is a promoter, etc. Further, by bringing the component (i) into contact with the component (ii-2), an effect of improving the molecular weight can be exhibited in addition to the effect described above. The preliminary contact temperature is usually from −20° C. to 200° C., preferably from −10° C. to 150° C., more preferably from 0° C. to 80° C. In the preliminary contact, an aliphatic hydrocarbon, an aromatic hydrocarbon, or the like can be used as an inert hydrocarbon serving as a solvent. Among these, an aliphatic hydrocarbon is particularly preferred.

It is desired that the use proportion of the catalyst component (i) to the catalyst component (iii) is in the range of preferably 1:1 to 1:10,000, more preferably 1:5 to 1:2,000, further more preferably 1:10 to 1:1,000 in terms of molar ratio. By using the catalyst component (iii), the polymerization activity per transition metal can be improved, however, if the amount thereof is too much, the organic aluminum compound is not only wasted, but also remains in a large amount in the polymer, and therefore, the excessive amount thereof is not preferred.

In the present invention, at least one of the catalyst components can be carried on a suitable carrier and used. The type of the carrier is not particularly limited, and any of an inorganic oxide carrier, an inorganic carrier other than the inorganic oxide carrier, and an organic carrier can be used. However, in particular, an inorganic oxide carrier or an inorganic carrier other than the inorganic oxide carrier is preferred.

Specific examples of the inorganic oxide carrier include $SiO_2$, $Al_2O_3$, MgO, $ZrO_2$, $TiO_2$, $Fe_2O_3$, $B_2O_3$, CaO, ZnO, BaO, $ThO_2$, and mixtures thereof such as silica alumina, zeolite, ferrite, and glass fiber. Among these, $SiO_2$ and $Al_2O_3$ are particularly preferred. The inorganic oxide carrier described above may contain a small amount of a carbonate, a nitrate, a sulfate, or the like.

On the other hand, examples of the carrier other than those described above include magnesium compounds represented by the general formula: $MgR^{17}_x X^1_y$ typified by $MgCl_2$, $Mg(OC_2H_5)_2$, and the like, and complex salts thereof. Here, $R^{17}$ represents an alkyl group having 1 to 20 carbon atoms, an alkoxy group having 1 to 20 carbon atoms, or an aryl group having 6 to 20 carbon atoms, $X^1$ represents a halogen atom or an alkyl group having 1 to 20 carbon atoms, x is 0 to 2, y is 0 to 2, and x+y=2. The respective $R^{17}$'s or the respective $X^1$'s may be the same as or different from each other.

Further, examples of the organic carrier include polymers such as polystyrene, styrene-divinylbenzene copolymers, polyethylene, poly(l-butene), substituted polystyrene, and polyallylate, as well as starch and carbon.

As the carrier to be used in the production method described above, $MgCl_2$, $MgCl(OC_2H_5)$, $Mg(OC_2H_5)_2$, $SiO_2$, $Al_2O_3$, and the like are preferred. The properties of the carrier vary depending on the type thereof and the production method, however, the average particle diameter is usually from 1 to 300 μm, preferably from 10 to 200 μm more preferably from 20 to 100 μm.

If the particle diameter is small, a fine powder in the polymer increases, and if the particle diameter is large, a coarse particle in the polymer increases to cause a reduction in the bulk density or the clogging of a hopper.

The carrier has a specific surface area of usually 1 to 1,000 m$^2$/g, preferably 50 to 500 m$^2$/g, and a pore volume of usually 0.1 to 5 cm$^3$/g, preferably 0.3 to 3 cm$^3$/g.

If either of the specific surface area and the pore volume deviates from the above range, the catalyst activity decreases in some cases. The specific surface area and the pore volume can be determined, for example, from the volume of adsorbed nitrogen gas according to a BET method.

Further, in the case where the carrier is an inorganic oxide carrier, it is desired that the carrier is preferably used after it is fired at usually 150 to 1,000° C., preferably 200 to 800° C.

In the case where at least one of the catalyst components is carried on the carrier described above, it is desired to carry at least one of the catalyst component (i) and the catalyst component (ii), preferably both of the catalyst component (i) and the catalyst component (ii) on the carrier.

The method for carrying at least one of the component (i) and the component (ii) on the carrier is not particularly limited, however, for example,
(1) a method in which at least one of the component (i) and the component (ii) is mixed with the carrier,
(2) a method in which the carrier is treated with an organic aluminum compound or a halogen-containing silicon compound, and then at least one of the component (i) and the component (ii) is mixed therewith in an inert solvent,
(3) a method in which the carrier, the component (i) and/or the component (ii), and an organic aluminum compound or a halogen-containing silicon compound are reacted with one another,
(4) a method in which the component (i) or the component (ii) is carried on the carrier, and then the component (ii) or the component (i) is mixed therewith,
(5) a method in which a catalytic reaction product of the component (i) and the component (ii) is mixed with the carrier,
(6) a method in which the carrier is allowed to coexist in the catalytic reaction of the component (i) and the component (ii), or the like can be used.

In the reactions in the above (4), (5), and (6), it is also possible to add the organic aluminum compound as the component The catalyst may be prepared by irradiation with an elastic wave when the components (i), (ii), and (iii) described above are brought into contact. As the elastic wave, generally a sonic wave, particularly preferably an ultrasonic wave can be used. To be specific, an ultrasonic wave with a frequency of 1 to 1,000 kHz, preferably an ultrasonic wave with a frequency of 10 to 500 kHz can be used.

The catalyst thus obtained may be used for polymerization after the solvent is evaporated off and the catalyst in the form of a solid is taken out or may be used for polymerization as it is.

Further, in the present invention, the catalyst can be produced by performing an operation of carrying at least one of the component (i) and the component (ii) on the carrier in the polymerization system. For example, a method in which at least one of the component (i) and the component (ii), and the carrier, and, if necessary, the organic aluminum compound as the component (iii) are added, and an olefin such as ethylene is added at an atmospheric pressure to 2 MPa (gauge) to carry out preliminary polymerization at −20 to 200° C. for about one minute to two hours, thereby forming catalyst particles can be used.

In the present invention, it is desired that the use proportion of the component (ii-1) to the carrier is preferably from 1:5 to 1:10,000, more preferably from 1:10 to 1:500 in terms of mass ratio, and the use proportion of the component (ii-2) to the carrier is preferably from 1:0.5 to 1:1,000, more preferably from 1:1 to 1:50 in terms of mass ratio. In the case where two or more components as the components (ii) are mixed and used, it is desired that the use proportion of each of the components (ii) to the carrier is in the above range in terms of mass ratio. Further, it is desired that the use proportion of the component (i) to the carrier is preferably from 1:5 to 1:10,000, more preferably from 1:10 to 1:500 in terms of mass ratio.

If the use proportion of the component (ii) [the component (ii-1) or the component (ii-2)] to the carrier or the use proportion of the component (i) to the carrier deviates from the above range, the activity decreases in some cases. The thus prepared polymerization catalyst of the present invention has an average particle diameter of usually 2 to 200 μm, preferably 10 to 150 μm, particularly preferably 20 to 100 μm, and has a specific surface area of usually 20 to 1,000 m²/g, preferably 50 to 500 m²/g. If the average particle diameter is less than 2 μm, a fine powder in the polymer increases in some cases, and if the average particle diameter exceeds 200 μm, a coarse particle in the polymer increases in some cases. If the specific surface area is less than 20 m²/g, the activity decreases in some cases, and if the specific surface area exceeds 1,000 m²/g, the bulk density of the polymer decreases in some cases. Further, in the catalyst of the present invention, the amount of the transition metal in 100 g of the carrier is usually from 0.05 to 10 g, particularly preferably from 0.1 to 2 g. If the amount of the transition metal is out of the above range, the activity decreases in some cases.

An industrially advantageous polymer having a high bulk density and an excellent particle size distribution can be obtained by carrying the catalyst on the carrier in the manner described above.

As the propylene-based polymer (A), by using the polymerization catalyst described above, a propylene homopolymer can be produced by homopolymerization of propylene, or a propylene copolymer can be produced by copolymerization of propylene and ethylene and/or an α-olefin having 4 or more carbon atoms.

In this case, the polymerization method is not particularly limited, and any method such as a slurry polymerization method, a gas-phase polymerization method, a bulk polymerization method, a solution polymerization method, or a suspension polymerization method may be used, however, a slurry polymerization method and a gas-phase polymerization method are particularly preferred. Further, from the viewpoint of the ease of control of the reaction, a solution polymerization method is particularly preferred.

With respect to the polymerization conditions, the polymerization temperature is usually from −100 to 250° C., preferably from −50 to 200° C., more preferably from 0 to 130° C. With respect to the use proportion of the catalyst to the reaction starting material, the starting material monomer/the component (A) described above (molar ratio) is preferably from $10^5$ to $10^8$, particularly preferably from $10^6$ to $10^7$. The polymerization time is usually from 5 minutes to 10 hours, and the reaction pressure is preferably from an atmospheric pressure to 3 MPa (gauge), more preferably from an atmospheric pressure to 2.5 MPa (gauge), further more preferably from an atmospheric pressure to 2 MPa (gauge). By adjusting the reaction pressure, the meso pentad fraction can be controlled.

Examples of the method for controlling the molecular weight of the polymer include selection of the type of the respective catalyst components, the use amount, or the polymerization temperature, and polymerization in the presence of hydrogen.

In the case of using a polymerization solvent, for example, an aromatic hydrocarbon such as benzene, toluene, xylene, or ethylbenzene, an alicyclic hydrocarbon such as cyclopentane, cyclohexane, or methylcyclohexane, an aliphatic hydrocarbon such as pentane, hexane, heptane, or octane, a halogenated hydrocarbon such as chloroform or dichloromethane, or the like can be used. Among these solvents, one type may be used alone or two or more types may be used in combination. Further, a monomer such as an α-olefin may be used as the solvent. The polymerization can be carried out without using a solvent depending on the polymerization method.

In the polymerization, preliminary polymerization can be carried out using the polymerization catalyst described above. The preliminary polymerization can be carried out by bringing, for example, a small amount of an olefin into contact with the solid catalyst component. However, the method is not particularly limited, and a known method can be used. The olefin to be used for the preliminary polymerization is not particularly limited, and for example, ethylene, an α-olefin having 3 to 20 carbon atoms, a mixture thereof, or the like can be used. However, it is advantageous to use the same olefin as used in the polymerization.

The preliminary polymerization temperature is usually from −20 to 200° C., preferably from −10 to 130° C., more preferably from 0 to 80° C. In the preliminary polymerization, an aliphatic hydrocarbon, an aromatic hydrocarbon, a monomer, or the like can be used as a solvent. Among these, an aliphatic hydrocarbon is particularly preferred. The preliminary polymerization may be carried out without using a solvent.

In the preliminary polymerization, it is desired to control the conditions so that the limiting viscosity [η] (measured in decalin at 135° C.) of the preliminary polymerization product is 0.2 dL/g or more, particularly 0.5 dL/g or more, and the amount of the preliminary polymerization product per millimole of the transition metal component in the catalyst is from 1 to 10,000 g, particularly from 10 to 1,000 g.

The base polymer for a hot-melt adhesive of the present invention may contain as the propylene-based polymer (A), only one type of propylene homopolymer, but may contain a mixture of two or more types of propylene homopolymers having different molecular weights, stereoregularities, or the like. In particular, the glass transition temperature of the propylene-based polymer is higher than that of a commercially available ethylene-based copolymer (Tg=−10 to −20° C.), and on the other hand, an ethylene-based polymer is liable to form a gelled material (particle) which is a cause of decreasing the physical properties, and therefore, from the viewpoint of the reduction of the blending amount of a tackifier resin or from the viewpoint of prevention of the formation of a gelled material (particle), the base polymer for a hot-melt adhesive of the present invention preferably contains a mixture of two or more types of propylene homopolymers as the propylene-based polymer (A).

In order to obtain an excellent solidification rate, it is preferred that the base polymer for a hot-melt adhesive of the present invention is a blend of 1 to 99 parts by mass of a propylene homopolymer (a) having a meso pentad fraction (mmmm) of 1 to 45 mol % and 99 to 1 part by mass of a propylene homopolymer (b) having a meso pentad fraction (mmmm) of 46 to 80 mol %, and the total amount of the propylene homopolymer (a) and the propylene homopolymer (b) is 100 parts by mass.

In order to obtain an excellent solidification rate and excellent adhesiveness, the blend is more preferably a blend of 10 to 90 parts by mass of the propylene homopolymer (a) and 90 to 10 parts by mass of the propylene homopolymer (b), further more preferably a blend of 20 to 80 parts by mass of the propylene homopolymer (a) and 80 to 20 parts by mass of the propylene homopolymer (b), still further more preferably a blend of 30 to 70 parts by mass of the propylene homopolymer (a) and 70 to 30 parts by mass of the propylene homopolymer (b). However, the total amount of the propylene homopolymer (a) and the propylene homopolymer (b) is 100 parts by mass.

In order to obtain an excellent solidification rate and excellent adhesiveness, the meso pentad fraction (mmmm) of the propylene homopolymer (a) is preferably from 10 to 45 mol %, more preferably from 20 to 45 mol %, further more preferably from 30 to 45 mol %. Further, in order to obtain an excellent solidification rate, the meso pentad fraction (mmmm) of the propylene homopolymer (a) is preferably from 1 to 30 mol %, more preferably from 3 to 20 mol %, further more preferably from 3 to 10 mol %.

The weight-average molecular weight of the propylene homopolymer (a) is preferably from 10,000 to 150,000, more preferably from 20,000 to 150,000, further more preferably from 20,000 to 120,000, still further more preferably from 20,000 to 100,000, yet still further more preferably from 20,000 to 80,000, most preferably from 30,000 to 60,000, from the viewpoint of the adhesive strength between non-woven cloths.

The molecular weight distribution (Mw/Mn) of the propylene homopolymer (a) is preferably 2.5 or less, more preferably 2.4 or less, further more preferably 2.3 or less, and also, for example, 1.2 or more, preferably 1.5 or more, from the viewpoint of the adhesive strength between non-woven cloths.

The melting endothermic amount (ΔH-D) of the propylene homopolymer (a) obtained by using a differential scanning calorimeter, and keeping 10 mg of a sample in a nitrogen atmosphere at −10° C. for 5 minutes, and then raising the temperature at 10° C./min is preferably 0 or more and less than 35, more preferably from 0 to 32, from the viewpoint of the adhesive strength between non-woven cloths.

The glass transition temperature (Tg) of the propylene homopolymer (a) is preferably from −20 to 10° C., more preferably from −10 to 10° C., further more preferably from −5 to 5° C., from the viewpoint of the adhesive strength between non-woven cloths.

The limiting viscosity [η] of the propylene homopolymer (a) is preferably from 0.01 to 2.0 dL/g, more preferably from 0.1 to 1.5 dL/g, further more preferably from 0.2 to 1.0 dL/g, from the viewpoint of the adhesive strength between non-woven cloths.

In order to obtain an excellent solidification rate, the meso pentad fraction (mmmm) of the propylene homopolymer (b) is more preferably from 50 to 80 mol %, further more preferably from 55 to 75 mol %, still further more preferably from 60 to 70 mol %.

The weight-average molecular weight of the propylene homopolymer (b) is preferably from 10,000 to 150,000, more preferably from 20,000 to 150,000, further more preferably from 20,000 to 120,000, still further more preferably from 20,000 to 100,000, yet still further more preferably from 20,000 to 80,000, most preferably from 30,000 to 60,000, from the viewpoint of the adhesive strength between non-woven cloths.

The molecular weight distribution (Mw/Mn) of the propylene homopolymer (b) is preferably 2.5 or less, more preferably 2.4 or less, further more preferably 2.3 or less, and also, for example, 1.2 or more, preferably 1.5 or more, from the viewpoint of the adhesive strength between non-woven cloths.

The melting endothermic amount (ΔH-D) of the propylene homopolymer (b) obtained by using a differential scanning calorimeter, and keeping 10 mg of a sample in a nitrogen atmosphere at −10° C. for 5 minutes, and then raising the temperature at 10° C./min is preferably from 35 to 80, more preferably from 35 to 70, from the viewpoint of the solidification rate.

The glass transition temperature (Tg) of the propylene homopolymer (b) is preferably from −20 to 10° C., more preferably from −10 to 10° C., further more preferably from −5 to 5° C., from the viewpoint of the adhesive strength between non-woven cloths.

The limiting viscosity [η] of the propylene homopolymer (b) is preferably from 0.01 to 2.0 dL/g, more preferably from 0.1 to 1.5 dL/g, further more preferably from 0.2 to 1.0 dL/g, from the viewpoint of the adhesive strength between non-woven cloths.

(Weight-Average Molecular Weight of Base Polymer)

The weight-average molecular weight of the base polymer for a hot-melt adhesive of the present invention is preferably from 5,000 to 150,000, more preferably from 10,000 to 100,000, further more preferably from 20,000 to 80,000, still further more preferably from 40,000 to 60,000 in terms of polypropylene, from the viewpoint of achieving both adhesiveness between non-woven cloths and adhesiveness between a film and a non-woven cloth.

The weight-average molecular weight of the base polymer for a hot-melt adhesive of the present invention is measured by the method described in Examples.

The weight-average molecular weight of the base polymer for a hot-melt adhesive of the present invention can be adjusted within a desired range by changing the polymerization conditions (a reaction temperature, a reaction time, a catalyst, or a promoter) of a propylene-based polymer (A), or by adding an additive, or by mixing two or more types of propylene-based polymers having different molecular weights.

(Molecular Weight Distribution of Base Polymer)

The molecular weight distribution (Mw/Mn) of the base polymer for a hot-melt adhesive of the present invention is preferably 4.5 or less, more preferably 4.0 or less, further more preferably 3.0 or less, still further more preferably 2.5 or less, from the viewpoint of coatability and also from the viewpoint of achieving both adhesiveness between non-woven cloths and adhesiveness between a film and a non-woven cloth.

The molecular weight distribution of the base polymer for a hot-melt adhesive of the present invention can be adjusted within a desired range by changing the polymerization conditions (a reaction temperature, a reaction time, a catalyst, or a promoter) of a propylene-based polymer (A), or by adding an additive, or by mixing two or more types of propylene-based polymers having different molecular weights.

(Glass Transition Temperature of Base Polymer)

It is generally said that the glass transition temperature (Tg) of a hot-melt adhesive is often adjusted to around room temperature. In the case where the glass transition temperature of the base polymer is low, a tackifier resin (tackifier) which plays a role in increasing the glass transition temperature is blended therein in a large amount.

The glass transition temperature of the base polymer for a hot-melt adhesive of the present invention is preferably higher from the viewpoint of decreasing the blending amount of the tackifier resin. Specifically, the glass transition temperature thereof is preferably from −10 to 10° C., more preferably around 0° C.

The glass transition temperature of the base polymer for a hot-melt adhesive of the present invention is measured by using a differential scanning calorimeter (DSC), and specifically measured by the method described in Examples. In the case where the base polymer has two glass transition temperatures, the glass transition temperatures preferably include around 0° C.

[Hot-Melt Adhesive]

The hot-melt adhesive of the present invention contains the above-mentioned base polymer, and may contain a tackifier resin (B) and an oil (C) as needed.

Further, the hot-melt adhesive of the present invention may contain a variety of additives such as a plasticizer, a wax, an inorganic filler, and an antioxidant as needed.

In particular, the base polymer of the present invention has excellent applicability to a hot-melt adhesive and can be used for controlling the solidification rate or the melt viscosity. In addition, the improvement of handleability and the like owing to the prevention of bleeding (seepage) of an oil, suppression of sticky feeling, etc. can be obtained. For example, it is considered that when a base polymer having a low modulus of elasticity in tension is added, the open time can be prolonged, and when a base polymer having a high modulus of elasticity in tension is added, the set time can be shortened.

The content of the base polymer with respect to the total amount of the hot-melt adhesive is preferably from 1 to 99% by mass, more preferably from 10 to 90% by mass, further more preferably from 20 to 80% by mass, still further more preferably from 30 to 70% by mass, yet still further more preferably from 30 to 60% by mass.

(Tackifier Resin (B))

Examples of the tackifier resin (B) include materials which are composed of a hydrogenated derivative of an aliphatic petroleum hydrocarbon resin, a rosin derivative resin, a polyterpene resin, a petroleum resin, an oil-soluble phenolic resin, or the like and are in the form of a solid, a semi-solid, or a liquid at normal temperature. Among these materials, one type may be used alone or two or more types may be used in combination. In the present invention, in consideration of the compatibility with the base polymer, it is preferred to use a hydrogenated material. In particular, a hydrogenated petroleum resin material having excellent heat stability is more preferred.

Examples of commercially available products of the tackifier resin (B) include I-MARV P-125, I-MARV P-100, and I-MARV P-90 (all manufactured by Idemitsu Kosan Co., Ltd.), Yumex 1001 (manufactured by Sanyo Chemical Industries, Ltd.), Hi-Rez T 1115 (manufactured by Mitsui Chemicals, Incorporated), Clearon K 100 (manufactured by Yasuhara Chemical Co., Ltd.), ECR 227, Escorez 2101, and Escorez 5000 series (all manufactured by Tonex Co., Ltd.), Arkon P100 (manufactured by Arakawa Chemical Industries, Ltd.), and Regalrez 1078 (manufactured by Hercules, Inc.) (all are trade names).

From the viewpoint of the improvement of the adhesiveness and also the improvement of the coatability and the wettability to an adherend due to a decrease in the viscosity, the content of the tackifier resin (B) in the hot-melt adhesive of the present invention is preferably from 50 to 200 parts by mass, more preferably from 50 to 150 parts by mass, further more preferably from 50 to 120 parts by mass with respect to 100 parts by mass of the base polymer.

(Oil (C))

Examples of the oil (C) include paraffin-based process oils and naphthene-based process oils. Examples of commercially available products of the oil (C) include Diana Process Oil PW-90 (trade name, manufactured by Idemitsu Kosan Co., Ltd.).

From the viewpoint of the improvement of the adhesiveness and also the improvement of the coatability and the wettability to an adherend due to a decrease in the viscosity, the content of the oil (C) in the hot-melt adhesive of the present invention is preferably from 10 to 200 parts by mass, more preferably from 20 to 150 parts by mass, further more preferably from 40 to 100 parts by mass with respect to 100 parts by mass of the base polymer.

(Additives)

Examples of the plasticizer include waxes, phthalate esters, adipate esters, fatty acid esters, glycols, and epoxy-based polymer plasticizers.

Examples of the waxes include animal waxes, vegetable waxes, carnauba waxes, candelilla waxes, Japan waxes, beeswaxes, mineral waxes, petroleum waxes, paraffin waxes, microcrystalline waxes, petrolatum, higher fatty acid waxes, higher fatty acid ester waxes, and Fischer-Tropsch waxes.

Examples of the inorganic filler include clay, talc, calcium carbonate, and barium carbonate.

Examples of the antioxidant include phosphorus-based antioxidants such as tris(nonylphenyl) phosphite, distearyl pentaerythritol diphosphite, Adekastab 1178 (manufactured by Adeka Corporation), Sumilizer TNP (manufactured by Sumitomo Chemical Co., Ltd.), Irgafos 168 (manufactured by BASF Co., Ltd.), and Sandstab P-EPQ (manufactured by Sandoz K.K.), phenolic antioxidants such as 2,6-di-t-butyl-4-methylphenol, n-octadecyl-3-(3',5'-di-t-butyl-4'-hydroxyphenyl)propionate, Sumilizer BHT (manufactured by Sumitomo Chemical Co., Ltd.), and Irganox 1010 (manufactured by BASF Co., Ltd.), and sulfur-based antioxidants such as dilauryl-3,3'-thiodipropionate, pentaerythritoltetrakis(3-laurylthiopropionate), Sumilizer TPL (manufactured by Sumitomo Chemical Co., Ltd.), Yoshinox DLTP (manufactured by Yoshitomi Pharmaceutical Industries, Ltd.), and AntiOx L (manufactured by NOF Corporation).

(Production Method for Hot-Melt Adhesive)

The hot-melt adhesive of the present invention can be produced by dry-blending the base polymer for a hot-melt adhesive of the present invention, and further according to need, the tackifier resin (B), the oil (C), and a variety of additives using a Henschel mixer or the like, and melt-kneading the components using a single-screw or twin-screw extruder, a Plastomill, a Banbury mixer, or the like.

The hot-melt adhesive of the present invention can be favorably used as an adhesive for sanitary articles such as pants type diapers, and also as an adhesive for woodwork, packaging, bookbinding, fibers, electrical materials, canning, building, bag making, and the like.

(Sanitary Article)

The sanitary article of the present invention is a sanitary article obtained by using the hot-melt adhesive, and is, for example, a sanitary article obtained by using the hot-melt adhesive when bonding non-woven cloths constituting the sanitary article, and/or when bonding a plastic film and a non-woven cloth constituting the sanitary article.

The sanitary article is preferably a non-woven cloth product, more specific examples thereof include tape type diapers, pants type diapers, pantiliners, and sanitary napkins, and preferred examples thereof include pants type diapers and pantiliners.

(Bonding Method)

The bonding method of the present invention is a method for bonding a substrate to another substrate, and includes a step of melting the hot-melt adhesive of the present invention and coating the adhesive onto at least one substrate, and a step of bonding the other substrate to the coated hot-melt adhesive.

EXAMPLES

Next, the present invention will be more specifically described with reference to Examples, but the present invention is by no means limited to these examples.

Synthesis Example 1

Production of Complex A ((1,1'-ethylene)(2,2'-tetramethyldisilylene)bisindenylzirconium dichloride)

Magnesium (12 g, 500 mmol) and tetrahydrofuran (30 mL) were put into a 500-mL two-necked flask, and 1,2-dibromoethane (0.2 mL) was added dropwise thereto to activate magnesium. 2-Bromoindene (20 g, 103 mmol) dissolved in tetrahydrofuran (150 mL) was added dropwise thereto, followed by stirring at room temperature for 1 hour. Subsequently, 1,2-dichlorotetramethyldisilane (9.4 mL, 5.1 mmol) was added dropwise thereto at 0° C. After the reaction mixture was stirred at room temperature for 1 hour, the solvent was evaporated off, and the residue was extracted with hexane (150 mL, twice), whereby 1,2-di(1H-inden-2-yl)-1,1,2,2-tetramethyldisilane was obtained as a white solid (15.4 g, 44.4 mmol, yield: 86%).

This solid was dissolved in diethyl ether (100 mL), then n-butyllithium (2.6 mol/L, 38 mL, 98 mmol) was added dropwise thereto at 0° C., followed by stirring at room temperature for 1 hour, resulting in precipitation of a white powder. The supernatant was removed, and the solid was washed with hexane (80 mL), whereby a lithium salt was obtained as a white powdery solid (14.6 g, 33.8 mmol, 76%).

This solid was dissolved in tetrahydrofuran (120 mL), and 1,2-dibromoethane (2.88 mL, 33.8 mmol) was added dropwise thereto at −30° C. The reaction mixture was stirred at room temperature for 1 hour, followed by evaporation to dryness, and the residue was extracted with hexane (150 mL), whereby a double-crosslinked ligand was obtained as a colorless oily liquid (14.2 g, 37.9 mmol).

This liquid was dissolved in diethyl ether (120 mL), and n-butyllithium (2.6 mol/L, 32 mL, 84 mmol) was added dropwise thereto at 0° C., followed by stirring at room temperature for 1 hour, resulting in precipitation of a white powder. The supernatant was removed, and the solid was washed with hexane (70 mL), whereby a lithium salt of the double-crosslinked ligand was obtained as a white powder (14.0 g, 31 mmol, yield: 81%).

A toluene (30 mL) suspension of zirconium tetrachloride (1.52 g, 6.54 mmol) was added dropwise at −78° C. to a toluene (30 mL) suspension of the obtained lithium salt of the double-crosslinked ligand (3.00 g, 6.54 mmol) through a cannula. The reaction mixture was stirred at room temperature for 2 hours, then the supernatant was separated, and further the residue was extracted with toluene.

Under reduced pressure, the supernatant and the solvent of the extract were evaporated off to dryness, whereby (1,1'-ethylene)(2,2'-tetramethyldisilylene)bisindenylzirconium dichloride represented by the following formula (1) was obtained as a yellow solid (2.5 g, 4.7 mmol, yield: 72%).

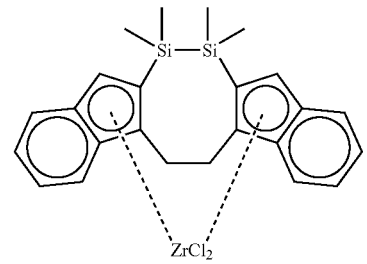

(1)

The measurement results of $^1$H-NMR are shown below.

$^1$H-NMR (CDCl$_3$): δ 0.617 (s, 6H, —SiMe$_2$-), 0.623 (s, 6H, —SiMe$_2$-), 3.65-3.74, 4.05-4.15 (m, 4H, CH$_2$CH$_2$), 6.79 (s, 2H, CpH), 7.0-7.5 (m, 8H, Aromatic-H)

Synthesis Example 2

Production of Complex B ((1,2'-dimethylsilylene)(2,1'-dimethylsilylene)-bis(3-trimethylsilylmethylindenyl)zirconium dichloride)

(1,2'-Dimethylsilylene)(2, 1'-dimethylsilylene)-bis(3-trimethylsilylmethylindenyl)zirconium dichloride) was synthesized according to the description of Reference Example 1 of Japanese Patent No. 4053993.

Synthesis Example 3

Production of Complex C ((1,2'-methylphenylsilylene)(2, 1'-methylphenylsilylene)-bis(3-trimethylsilylmethylindenyl)zirconium dichloride)

<Preparation of LDA>

Diisopropylamine (36 mL, 260 mmol) and THF (180 mL) were put into a 500-mL Schlenk, and cooled to about −70° C. with dry ice/ethanol, and then, butyllithium (91 mL, 245 mmol) was added dropwise thereto. After completion of dropwise addition, the temperature of the resulting mixture was raised to room temperature and the mixture was used for a reaction.

<Synthesis of Ind-SiMePhCl>

Magnesium (20.0 g, 833 mmol) and THF (250 mL) were put into a 2-L three-necked flask, and 1,2-dibromoethane (1.0 mL) was added thereto, followed by stirring at room temperature for 15 minutes to activate the surface of magnesium. A solution of 2-bromoindene (78.3 g, 401 mmol) in THF (250 mL) was added dropwise thereto using a constant pressure dropping funnel. After completion of dropwise addition, the resulting mixture was stirred at room temperature for 30 minutes. The thus obtained Grignard solution was cooled using an ice bath, and dichloromethylphenylsilane (65.0 mL, 400 mmol) was added thereto, and the resulting mixture was returned to room temperature and then stirred for 30 minutes. The reaction mixture was evaporated, and sufficiently dried under vacuum, followed by extraction with hexane (1 L). Then, the hexane solution was evaporated, whereby Ind-SiMePhCl was obtained as a light yellow oil (101 g, 372 mmol). This oil was distilled under reduced pressure, whereby high purity Ind-SiMePhCl was obtained (66.3 g, 245 mmol, 66%).

The measurement results of $^1$H-NMR are shown below.

$^1$H-NMR (CDCl$_3$): δ 0.920 (s, 3H, SiMe), δ3.60 (2H, IndH$_2$), δ 7.3-7.7 (5H, aromatics)

<Synthesis of 2Li$^+$[(Ind)$_2$(SiMePh)$_2$]$^{2-}$>

Ind-SiMePhCl was dissolved in THF (180 mL), followed by cooling in an ice bath, and then, LDA (245 mmol) was added dropwise thereto using a constant pressure dropping funnel. The reaction mixture was stirred for 20 hours while keeping the reaction mixture cool in the ice bath, and thereafter, the temperature of the mixture was raised to room temperature, and the solvent was evaporated off under vacuum. The obtained foamy solid was extracted with hexane (500 mL, twice), whereby (Ind)$_2$(SiMePh)$_2$ was obtained as a white foamy solid (40.0 g, 85.5 mmol, 70%).

The thus obtained (Ind)$_2$(SiMePh)$_2$ was dissolved in diethyl ether (220 mL), followed by cooling to 0° C. in an ice bath, and then, butyllithium (67.0 mL, 181 mmol) was added dropwise thereto. The temperature of the resulting mixture was raised to room temperature, followed by stirring for 15 minutes, resulting in a white precipitate. The white precipitate and the supernatant solution were separated using a cannula, and the supernatant was evaporated to dryness, and the resulting residue was washed with hexane, whereby 2Li$^+$[(Ind)$_2$(SiMePh)$_2$]$^{2-}$ was obtained (31.5 g, 51.2 mmol, 63%).

The measurement results of $^1$H-NMR are shown below.

$^1$H-NMR (THF-d$_8$): δ 0.844 (s, 6H, SiMe), δ 6.61 (s, 2H, IndH), δ 6.4-7.8 (8H, aromatics)

<Synthesis of (Ind-3-CH$_2$SiMe$_3$)$_2$(SiMePh)$_2$>

To 2Li$^+$[(Ind)$_2$(SiMePh)$_2$]$^{2-}$, THF (100 mL) was added, followed by cooling in an ice bath, and then, iodomethyltrimethylsilane (16.0 mL, 108 mmol) was added dropwise thereto. After completion of dropwise addition, the resulting mixture was stirred for 1 hour at room temperature, and then, ion exchanged water (30 mL) was added thereto, followed by quenching, and the organic layer was washed with a saturated aqueous ammonium chloride solution. The obtained organic layer was dehydrated with anhydrous magnesium sulfate, and the solvent was evaporated off, whereby (Ind-3-CH$_2$SiMe$_3$)$_2$(SiMePh)$_2$ was obtained as a yellow-brown viscous solid (32.4 g, 50.6 mmol, 99%).

<Synthesis of 2Li$^+$[(Ind-3-CH$_2$SiMe$_3$)$_2$(SiMePh)$_2$]$^{2-}$>

(Ind-3-CH$_2$SiMe$_3$)$_2$(SiMePh)$_2$ was dissolved in diethyl ether, followed by cooling in an ice bath, and then, n-butyllithium (40.0 mL, 106 mmol) was added dropwise thereto, and the resulting mixture was stirred at room temperature for 1 hour. From the obtained reaction mixture, the solvent was evaporated off, and the deposited solid was washed with hexane (50 mL), whereby 2Li$^+$[(Ind-3-CH$_2$SiMe$_3$)$_2$(SiMePh)$_2$]$^{2-}$ was obtained (19.3 g, 25.3 mmol, 50%).

Synthesis of (1,2'-methylphenylsilylene)(2,1'-methylphenylsilylene)-bis(3-trimethylsilylmethylindenyl)zirconium dichloride)$^-$>

2Li$^+$[(Ind-3-CH$_2$SiMe$_3$)$_2$(SiMePh)$_2$]$^{2-}$ was suspended in hexane, and the resulting suspension was cooled to −30° C. in a dry ice-ethanol bath, and a hexane suspension of zirconium tetrachloride (5.9 g, 25 mmol) was gradually added dropwise thereto with a cannula. After completion of dropwise addition, the resulting mixture was stirred overnight. The solvent was evaporated off from the organic layer and a hexane extract from the yellow residue, whereby (1,2'-methylphenylsilylene)(2,1'-methylphenylsilylene)-bis(3-trimethylsilylmethylindenyl)zirconium dichloride was obtained as a yellow powder (7.35 g, 9.24 mmol, 37%).

The measurement results of $^1$H-NMR are shown below.

$^1$H-NMR (CDCl$_3$): δ-0.07 (s, 18H, CH$_2$SiMe$_3$), δ 0.929 (s, 6H, SiMe), δ 2.26, 2.29 (d, 2H, CH$_2$SiMe$_3$) δ 2.71, 2.75 (d, 2H, CH$_2$SiMe$_3$), δ 6.9-7.5 (8H, aromatics)

Synthesis Example 4

Production of Complex D ((1,2'-dimethylsilylene)(2, 1'-dimethylsilylene)(indenyl)(3-trimethylsilylmethylindenyl)zirconium dichloride)

(1,2'-Dimethylsilylene)(2, 1'-dimethylsilylene)(indenyl)(3-trimethylsilylmethylindenyl)zirconium dichloride was synthesized according to the description of Example 5 of Japanese Patent No. 4053993.

Synthesis Example 5

Production of Complex E ((1,2'-dimethylsilylene)(2,1'-dimethylsilylene)-bis(indenyl)zirconium dichloride)

(1,2'-Dimethylsilylene)(2, 1'-dimethylsilylene)-bis(indenyl)zirconium dichloride was synthesized according to the description of Example 1 of JP-A 2000-256411.

Production Example 1

(Production of Polypropylene (1))

Heptane (4 L), triisobutylaluminum (2 M, 2 mL, 4 mmol), a heptane slurry of the complex A (2.0 mL, containing 20 µmol of the complex A), and a toluene solution of methylalumoxane manufactured by Albemarle Corporation (6.6 mL, containing 20 mmol of methylalumoxane) were added to a 10-L autoclave that had been dried by heating, and further, 0.01 MPa of hydrogen was introduced thereinto. Then, propylene was introduced thereinto until the total pressure reached 0.66 MPa while stirring, and at the same time, the temperature was raised to 50° C. After polymerization was carried out for 1.5 hours, the polymerization was stopped with 5 mL of ethanol, followed by depressurization. Then, the reaction product was dried under reduced pressure, whereby polypropylene (1) (830 g) was obtained.

Production Example 2

(Production of Polypropylene (2))

Decalin (4 L), triisobutylaluminum (2 M, 2 mL, 4 mmol), a heptane slurry of the complex B (0.3 mL, containing 3 µmol of the complex B), and a heptane slurry of dimethylanilinium tetrakis(pentafluorophenyl)borate (0.9 mL, containing 9.0 µmol of borate) were added to a 10-L autoclave that had been dried by heating, and further, 0.25 MPa of hydrogen was introduced thereinto. Then, propylene was introduced until the total pressure reached 0.86 MPa while stirring, and at the same time, the temperature was raised to 80° C. After polymerization was carried out for 2 hours, the polymerization was stopped with 5 mL of ethanol, followed by depressurization. Then, the reaction product was added to 10 of acetone, and the deposited polymer was dried under reduced pressure, whereby polypropylene (2) (1900 g) was obtained.

Production Example 3

(Production of Polypropylene (3))

Heptane (400 mL), triisobutylaluminum (2 M, 0.2 mL, 0.4 mmol), a heptane slurry of the complex C (10 µmol/mL, 0.04 mL, 0.4 µmol), and a heptane slurry of dimethylanilinium tetrakis(pentafluorophenyl)borate (10 µmol/mL, 0.12 mL, 1.2 µmol) were added to a 1-L autoclave that had been dried by heating, and further, 0.05 MPa of hydrogen was introduced thereinto. Then, the temperature was raised to 75° C. while stirring, and at the same time, propylene was introduced thereinto so that the total pressure reached 0.70 MPa, and polymerization was carried out for 60 minutes. After completion of the polymerization reaction, the polymerization was stopped with 5 mL of ethanol, and then, the reaction product was dried under reduced pressure, whereby polypropylene (3) (180 g) was obtained.

Production Example 4

(Production of Polypropylene (4))

Heptane (4 L), triisobutylaluminum (2 M, 2 mL, 4 mmol), a heptane slurry of the complex D (0.3 mL, containing 3 µmol of the complex C), and a heptane slurry of dimethylanilinium tetrakis(pentafluorophenyl)borate (10 µmol/mL, 0.9 mL, 9.0 µmol) were added to a 10-L autoclave that had been dried by heating, and further, 0.01 MPa of hydrogen was introduced thereinto. Then, propylene was introduced thereinto until the total pressure reached 0.66 MPa while stirring, and at the same time, the temperature was raised to 65° C. After polymerization was carried out for 3 hours, the polymerization was stopped with 5 mL of ethanol, followed by depressurization. Then, the reaction product was dried under reduced pressure, whereby polypropylene (4) (1410 g) was obtained.

Production Example 5

(Production of Polypropylene (5))

Heptane (4 L), triisobutylaluminum (2 M, 2 mL, 4 mmol), a heptane slurry of the complex E (10 µmol/mL, 0.3 mL, 3 µmol), and a heptane slurry of dimethylanilinium tetrakis(pentafluorophenyl)borate (10 µmol/mL, 0.9 mL, 9.0 µmol) were added to a 10-L autoclave that had been dried by heating, and further, 0.01 MPa of hydrogen was introduced thereinto. Then, propylene was introduced thereinto until the total pressure reached 0.66 MPa while stirring, and at the same time, the temperature was raised to 60° C. After polymerization was carried out for 2 hours, the polymerization was stopped with 5 mL of ethanol, followed by depressurization. Then, the reaction product was dried under reduced pressure, whereby polypropylene (5) (1390 g) was obtained.

Production Example 6

(Production of Polypropylene (6))

Heptane (400 mL), triisobutylaluminum (2 M, 0.2 mL, 0.4 mmol), a heptane slurry of the complex B (10 µmol/mL, 0.04 mL, 0.4 µmol), and a heptane slurry of dimethylanilinium tetrakis(pentafluorophenyl)borate (10 µmol/mL, 0.12 mL, 1.2 µmol) were added to a 1-L autoclave that had been dried by heating, and further, 0.05 MPa of hydrogen was introduced thereinto. Then, the temperature was raised to 58° C. while stirring, and at the same time, propylene was introduced thereinto so that the total pressure reached 0.70 MPa, and polymerization was carried out for 60 minutes. After completion of the polymerization reaction, the polymerization was stopped with 5 mL of ethanol, and then, the reaction product was dried under reduced pressure, whereby polypropylene (6) (230 g) was obtained.

[Evaluation of Stereoregularity: NMR Measurement]

With respect to the polypropylenes (1) to (6) obtained in the Production Examples 1 to 6, the $^{13}$C-NMR spectrum was measured using the following device under the following conditions. The assignment of a peak was carried out in accordance with the method proposed in "Macromolecules, 8, 687 (1975)" by A. Zambelli, et al. The results are shown in Table 1.

Device: $^{13}$C-NMR spectrometer, JNM-EX400 series manufactured by JEOL, Ltd.

Method: proton complete decoupling method

Concentration: 220 mg/mL

Solvent: a mixed solvent of 1,2,4-trichlorobenzene and deuterated benzene at 90:10 (volume ratio)

Temperature: 130° C.

Pulse width: 45°

Pulse repetition time: 4 seconds

Accumulation: 10,000 times

<Calculation Formulae>

M=m/S×100

R=γ/S×100

S=Pββ+Paβ+Paγ

S: signal intensity of carbon atoms of side-chain methyl in all propylene units

Pββ: 19.8 to 22.5 ppm

Paβ: 18.0 to 17.5 ppm

Paγ: 17.5 to 17.1 ppm

γ racemic pentad chain: 20.7 to 20.3 ppm m: meso pentad chain: 21.7 to 22.5 ppm

The meso pentad fraction [mmmm] and the racemic meso racemic meso pentad fraction [rmrm] are determined in accordance with the method proposed in "Macromolecules, 6, 925 (1973)" by A. Zambelli et al., and are a meso fraction and a racemic meso racemic meso fraction in a pentad unit in a polypropylene molecular chain measured with the signal of a methyl group in the $^{13}$C-NMR spectrum. The stereo-regularity increases with the increase in the meso pentad fraction [mmmm].

[Measurement of Weight-Average Molecular Weight (Mw) and Molecular Weight Distribution (Mw/Mn)]

With respect to the polypropylenes (1) to (6) obtained in the Production Examples 1 to 6, according to the gel permeation chromatography (GPC) method, the weight-average molecular weight (Mw) and the molecular weight distribution (Mw/Mn) were obtained. In the measurement, the following device was used under the following conditions, and the weight-average molecular weight in terms of polystyrene was obtained. The results are shown in Table 1.

<GPC Measuring Device>
Column: TOSO GMHHR-H(S)HT
Detector: RI detector for liquid chromatography, Waters 150 C <Measurement Conditions>
Solvent: 1,2,4-trichlorobenzene
Measurement temperature: 145° C.
Flow rate: 1.0 mL/min
Sample concentration: 2.2 mg/mL
Injection amount: 160 µL
Calibration curve: Universal Calibration
Analysis software: HT-GPC (ver. 1.0)

[Limiting Viscosity (η)]

With respect to the polypropylenes (1) to (6) obtained in the Production Examples 1 to 6, 0.02 to 0.16 g/dL solutions were subjected to measurement at 135° C. using a viscometer (manufactured by RIGO Co., Ltd., trade name: "VMR-053U-PC-F01"), an Ubbelohde type viscosity tube (bulb volume in measurement: 2 to 3 mL, capillary diameter: 0.44 to 0.48 mm), and tetralin as the solvent. The results are shown in Table 1.

[DSC Measurement]

With respect to the polypropylenes (1) to (6) obtained in the Production Examples 1 to 6, the melting endothermic amount obtained by using a differential scanning calorimeter (manufactured by PerkinElmer Co., Ltd., DSC-7), keeping 10 mg of a sample in a nitrogen atmosphere at −10° C. for 5 minutes, and then raising the temperature at 10° C./min was determined to be ΔAH-D and a glass transition temperature Tg. Further, from the peak top of a peak observed on the highest temperature side in the obtained melting endothermic curve, the melting point (Tm-D) was determined. The results are shown in Table 1.

Starting materials used in the production of the following base polymers for a hot-melt adhesive and hot-melt adhesives are shown.

<Tackifier Resin (B)>
A hydrogenated derivative of an aliphatic petroleum hydrocarbon resin (trade name: Escorez 5300, manufactured by Tonex Co., Ltd.)

<Oil (C)>
A paraffin-based process oil (trade name: Diana Process Oil PW-90, manufactured by Idemitsu Kosan Co., Ltd.)

Examples 1 to 3, Comparative Example 1

(Production of Base Polymer for Hot-Melt Adhesive)

The materials shown in Table 2 were melt-kneaded according to the blending ratios (mass ratios) shown in Table 2 using a batch-type Labo Plastomill at a kneading temperature of 200° C. and a screw rotation rate of 80 rpm for a kneading time of 5 minutes, whereby base polymers for a hot-melt adhesive were produced. With respect to the thus obtained base polymers for a hot-melt adhesive, the following evaluation was carried out.

<Modulus of Elasticity in Tension>
Each of the base polymers for a hot-melt adhesive shown in Table 2 was press-molded to prepare a test piece, and the modulus of elasticity in tension of the base polymer for a hot-melt adhesive was measured according to JIS K 7113 under the following conditions.
Test piece (No. 2 dumbbell), thickness: 1 mm
Cross head rate: 100 mm/min
Load cell: 100 N
Measurement temperature: 23° C.

<Semi-Crystallization Time>
By using a differential scanning calorimeter (manufactured by PerkinElmer Co., Ltd., trade name: DSC-8500), the measurement was carried out according to the following method.

Each of the base polymers for a hot-melt adhesive shown in Table 2 was melted by heating at 220° C. for 5 minutes, and then, cooled to 23° C. at 320° C./min. Then, a change over time of the calorific value during the isothermal crystallization at 23° C. was measured and the semi-crystallization time was determined.

<Tensile Elongation at Break>
Each of the base polymers for a hot-melt adhesive shown in Table 2 was press-molded to prepare a test piece, and the tensile elongation at break of the base polymers for a hot-melt adhesive was measured according to JIS K 7113 under the following conditions.
Test piece (JIS K 7113-No. 2, ½ size dumbbell), thickness: 1 mm
Measurement temperature: 23° C.
Tensile rate: 100 mm/min
Inter-chuck distance: 40 mm

TABLE 1

| | | Production Example | | | | | |
|---|---|---|---|---|---|---|---|
| | | 1 | 2 | 3 | 4 | 5 | 6 |
| Catalyst | | Complex A | Complex B | Complex C | Complex D | Complex E | Complex B |
| Polypropylene | | (1) | (2) | (3) | (4) | (5) | (6) |
| Meso pentad fraction (mmmm) | mol % | 5 | 41 | 44 | 60 | 70 | 48 |
| Limiting viscosity (η) | dl/g | 0.44 | 0.42 | 0.36 | 0.42 | 0.45 | 0.89 |
| Melting point (Tm-D) | ° C. | Not detected | 66.4 | 70.3 | 100.3 | 115.6 | 71.0 |
| Melting endothermic amount (ΔH-D) | J/g | 0 | 27.9 | 31.4 | 53.9 | 69.1 | 36.0 |
| Weight-average molecular weight Mw | | 50000 | 48000 | 44000 | 48000 | 52000 | 124000 |
| Mw/Mn | | 2.0 | 2.1 | 2.1 | 2.4 | 2.3 | 2.0 |
| Glass transition temperature Tg | ° C. | −3.5 | −4.7 | −3.3 | −3.1 | −4.5 | −4.1 |

TABLE 2

| Polypropylene | Meso pentad fraction (mol %) | Example 1 | Example 2 | Example 3 | Comparative Example 1 |
|---|---|---|---|---|---|
| Polypropylene (1) | 5 | 43 | 33 | — | — |
| Polypropylene (2) | 41 | — | — | 80 | 100 |
| Polypropylene (4) | 60 | — | 67 | — | — |
| Polypropylene (5) | 70 | 57 | — | 20 | — |
| Average meso pentad fraction (mol %) | | 42 | 42 | 47 | 41 |
| Modulus of elasticity in tension (MPa) | | 91 | 80 | 73 | 39 |
| Semi-crystallization time (min) | | 1 | 2.3 | 3.5 | 22.6 |
| Elongation at break (%) | | 500 | 610 | 630 | 680 |
| Weight-average molecular weight Mw | | 51000 | 49000 | 49000 | 48000 |
| Mw/Mn | | 2.4 | 2.4 | 2.3 | 2.1 |
| Glass transition temperature Tg (° C.) | | −3.6 | −3 | −4.7 | −4.7 |

Examples 4 to 5, Comparative Example 2

(Production of Hot-Melt Adhesive)

The materials shown in Table 3 were put into a sample bottle according to the blending ratios (mass ratios) shown in Table 3 and melted by heating at 180° C. for 30 minutes, followed by sufficiently mixing and stirring the materials with a rotary blade, whereby hot-melt adhesives were produced. With respect to the thus obtained hot-melt adhesives, the following evaluation was carried out. Incidentally, the base polymers used in Examples 4 and 5 both had (1) a modulus of elasticity in tension at 23° C. of 400 MPa or less, and (2) a semi-crystallization time at 23° C. of 20 minutes or less.

<T-Peel Strength>

A T-peel strength is an index indicating the strength of a bonding force, and as the strength is higher, peeling is less likely to occur, and therefore a higher T-peel strength is preferred.

Under the following conditions, a predetermined amount of the hot-melt adhesive was coated, and a polyethylene film (PE) and a non-woven cloth (NW) were bonded to each other, and also non-woven cloths were bonded to each other, and each of the bonded materials was cut to a width of 25 mm in the CD direction, whereby test pieces were prepared.

Line speed: 150 m/min
Coating amount: 3, 4, 5 g/m²
Spiral diameter: 15 mm
Coating temperature: 150° C.
Bonding pressure: 0.1 MPa The measurement of the T-peel strength was carried out according to the following method.

The hot-melt adhesive was coated onto an adherend at a coating temperature of 150° C., and the other adherend was overlaid thereon and pressed at a pressure of 1 MPa, whereby these adherends were bonded to each other. The thus obtained bonded sample was cut to a width of 25 mm in a direction (CD direction) perpendicular to the traveling direction of the substrate of the bonded sample, and the T-peel strength was measured. The measurement environment was as follows: 23° C. and 50% RH, the peeling speed was set to 100 mm/min, and an average of two maximum values was determined to be a peel strength value.

The peel strength value obtained when the sample was left to stand at room temperature (23° C.) for 1 hour after coating was defined as "T-peel after 1 h", the peel strength value obtained when the sample was left to stand at room temperature (23° C.) for 24 hours after coating was defined as "Initial T-peel", and the peel strength value obtained when the sample was left to stand at room temperature for 24 hours after a lapse of 2 weeks at 50° C. was defined as "Aging T-peel".

TABLE 3

| | | | | | Example 4 | Example 5 | Comparative Example 2 |
|---|---|---|---|---|---|---|---|
| Composition (parts by mass) | Base polymer (A) | Polypropylene (3) | mmmm = 44 | | 7.5 | — | — |
| | | Polypropylene (6) | mmmm = 48 | | 22.5 | — | — |
| | | Polypropylene (2) | mmmm = 41 | | — | 44 | 30 |
| | | Polypropylene (5) | mmmm = 70 | | — | 11 | — |
| | Tackifier resin (B) *1 | | | | 50 | 30 | 50 |
| | Oil (C) *2 | | | | 20 | 15 | 20 |
| PE/NW | Initial T-peel | | | 3 g/m² | 131 | 66 | 183 |
| | | | | 4 g/m² | 214 | 89 | 198 |
| | | | | 5 g/m² | 225 | 119 | 207 |
| | Aging T-peel | | | 3 g/m² | 83 | 46 | 235 |
| | | | | 4 g/m² | 131 | 74 | 226 |
| | | | | 5 g/m² | 156 | 83 | 224 |
| NW/NW | Initial T-peel | | | 3 g/m² | 294 | 389 | 88 |
| | | | | 4 g/m² | 383 | 546 | 108 |
| | | | | 5 g/m² | 520 | 620 | 123 |
| | Aging T-peel | | | 3 g/m² | 440 | 459 | 103 |
| | | | | 4 g/m² | 562 | 615 | 97 |
| | | | | 5 g/m² | 596 | 643 | 125 |
| NW/NW | T-peel after 1 h | | | 4 g/m² | 250 | 440 | 90 |
| | Reference: viscosity (mPa · s) at 160° C. | | | | 3260 | 3030 | 920 | mmmm: meso pentad fraction (mol %)

*1: A hydrogenated derivative of an aliphatic petroleum hydrocarbon resin (trade name: Escorez 5300, manufactured by Tonex Co., Ltd.)
*2: A paraffin-based process oil (trade name: Diana Process Oil PW-90, manufactured by Idemitsu Kosan Co., Ltd.)

(Production and Evaluation of Base Polymer for Hot-Melt Adhesive)

The materials shown in Table 4 were melt-kneaded according to the blending ratios (mass ratios) shown in Table 4 using a batch-type Labo Plastomill at a kneading temperature of 200° C. and a screw rotation rate of 80 rpm for a kneading time of 5 minutes, whereby a base polymer (A) for a hot-melt adhesive used in Example 4 was produced. With respect to the thus obtained base polymer for a hot-melt adhesive, evaluation was carried out in the same manner as in Example 1.

TABLE 4

| Polypropylene | Meso pentad fraction (mol %) | Example 4 |
|---|---|---|
| Polypropylene (3) | 44 | 25 |
| Polypropylene (6) | 48 | 75 |
| Average meso pentad fraction (mol %) | | 46 |
| Modulus of elasticity in tension (MPa) | | 85 |
| Semi-crystallization time (min) | | 12.8 |
| Elongation at break (%) | | 919 |
| Glass transition temperature Tg (° C.) | | −3.8 |

Table 3 shows that the hot-melt adhesive containing the base polymer for a hot-melt adhesive of the present invention not only has excellent adhesiveness between non-woven cloths, but also has excellent solidification rate. Further, it is found that Example 4 not only has excellent adhesiveness between non-woven cloths, but also has excellent adhesiveness between a polyethylene film and a non-woven cloth.

INDUSTRIAL APPLICABILITY

The hot-melt adhesive containing the base polymer for a hot-melt adhesive of the present invention not only has excellent adhesiveness between materials of the same type for example, adhesiveness between non-woven cloths), but also has excellent adhesiveness between materials of different types (for example, adhesiveness between a film and a non-woven cloth). Due to this, the hot-melt adhesive of the present invention can be favorable used as an adhesive for sanitary articles such as pants type diapers, and also as an adhesive for woodwork, packaging, bookbinding, fibers, electrical materials, canning, building, bag making, and the like.

The invention claimed is:

1. A base polymer for a hot-melt adhesive which satisfies the following (1) and (2):
   (1) a modulus of elasticity in tension at 23° C. is 200 MPa or less; and
   (2) a semi-crystallization time at 23° C. is 15 minutes or less,
   wherein the base polymer is a blend of
      1 to 99 parts by mass of a propylene homopolymer (a) having a meso pentad fraction (mmmm) of 1 to 45 mol % and
      99 to 1 part by mass of a propylene homopolymer (b) having a meso pentad fraction (mmmm) of 46 to 80 mol %, and
   the total amount of the propylene homopolymers (a) and (b) is 100 parts by mass.

2. The base polymer for a hot-melt adhesive according to claim 1, wherein the following (3) is satisfied:
   (3) an elongation at break at 23° C. is 150% or more and 1,000% or less.

3. The base polymer for a hot-melt adhesive according to claim 1, wherein a weight-average molecular weight is from 5,000 to 150,000.

4. The base polymer for a hot-melt adhesive according to claim 2, wherein a weight-average molecular weight is from 5,000 to 150,000.

5. A hot-melt adhesive, comprising the base polymer for a hot-melt adhesive according to claim 1.

6. The hot-melt adhesive according to claim 5, wherein the content of the base polymer for a hot-melt adhesive is from 1 to 90% by mass.

7. The hot-melt adhesive according to claim 5, further comprising a tackifier resin and an oil.

8. A hot-melt adhesive, comprising the base polymer for a hot-melt adhesive according to claim 2.

9. A hot-melt adhesive, comprising the base polymer for a hot-melt adhesive according to claim 3.

10. A sanitary article obtained by using the hot-melt adhesive according to claim 5.

11. A method for bonding a substrate to another substrate, comprising a step of melting the hot-melt adhesive according to claim 5 and coating the adhesive onto at least one substrate, and a step of bonding the other substrate to the coated hot-melt adhesive.

* * * * *